| United States Patent [19] | [11] | 4,440,940 |
| --- | --- | --- |
| Shepherd | [45] | Apr. 3, 1984 |

[54] ANTI-ATHEROSCLEROTIC AGENTS

[75] Inventor: Robert G. Shepherd, South Nyack, N.Y.

[73] Assignee: American Cyanamid Company, Stamford, Conn.

[21] Appl. No.: 323,522

[22] Filed: Nov. 19, 1981

Related U.S. Application Data

[63] Continuation of Ser. No. 85,652, Oct. 17, 1979, abandoned.

[51] Int. Cl.³ ............................................ C07C 101/00
[52] U.S. Cl. ...................................... 560/19; 560/48; 546/226; 548/238; 548/239; 548/335; 548/539; 562/433; 562/457; 562/458; 260/453 RW; 260/465 E; 260/500.5 SH; 260/544 N; 564/161; 564/162; 564/163; 564/305; 564/328; 424/305; 424/309; 424/319; 424/320
[58] Field of Search .............. 562/458, 433, 457, 458; 424/310, 319; 560/19, 48; 564/161, 162, 163, 308, 328

[56] References Cited

PUBLICATIONS

Vincent et al., Chem. Absts., 73, 66609(u), 1970.

Primary Examiner—Paul J. Killos
Attorney, Agent, or Firm—Charles E. Costello, Jr.

[57] ABSTRACT

This disclosure describes 2- or 3-[(unsaturated or cyclopropylated alkyl)amino]phenyl compounds and derivatives useful as hypolipidemic and antiatherosclerotic agents.

16 Claims, No Drawings

ANTI-ATHEROSCLEROTIC AGENTS

This is a continuation of application Ser. No. 85,652, filed Oct. 17, 1979 now abandoned.

BRIEF SUMMARY OF THE INVENTION

This invention relates to new organic compounds and more particularly, is concerned with novel 2- or 3-(alkenylamino, cyclopropylalkylamino, and alkynylamino)phenyl compounds and derivatives which may be represented by the following structural formula:

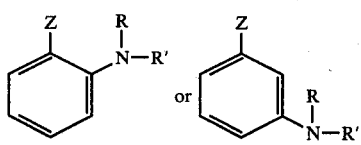

wherein R' is a branched or unbranched mono- or poly-unsaturated or cyclopropylated $C_3$-$C_{22}$ alkyl group and can be represented by the formula:

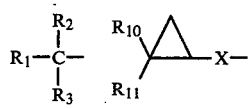

wherein $R_2$ and $R_3$ are the same or different and are hydrogen or a saturated or unsaturated $C_1$ to $C_9$ alkyl group;

Z is

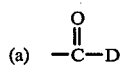

wherein D is selected from the group consisting of hydrogen, hydroxy, loweralkyl, a loweralkoxy group unsubstituted or substituted with one or more moieties selected from the group consisting of hydroxy, carboxyl, carboloweralkoxy, carboxamido, N,N-diloweralkylcarboxamido, cyano, diloweralkylamino, piperazino or polymethyleneimino (ring size 5–8) group; a benzyloxy group unsubstituted or substituted with at least one halogen or carboxy group; a phenoxy moiety unsubstituted or substituted with at least one halogen, carboxy, carboloweralkoxy loweralkyl, carboxamido, loweralkoxy or cyano group; or a 3-pyridyloxy group unsubstituted or substituted with a loweralkyl group, halogen, cyano, carboxyl, carboloweralkoxy, loweralkoxy or hydroxy group; and loweralkyl bearing one or more carboxy, carboloweralkoxy, carbamoyl, acyl, sulfinyl or sulfonyl groups;

wherein B is a saturated or unsaturated lower alkylene group and E is selected from the group consisting of hydrogen, loweralkyl, loweralkoxyethyl, diloweralkylaminoethyl, (mono- or polyhydroxy)loweralkyl, (mono- or polycarboxy)loweralkyl, (mono- or polycarboxy)hydroxyloweralkyl, allyl, 2,3-epoxypropyl, substituted or unsubstituted (phenyl, benzyl or 3-pyridyl), pyridylmethyl, and tetrahydropyranyl; or

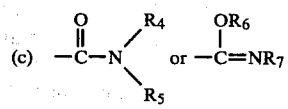

wherein $R_4$ is selected from the group consisting of hydrogen, carboxyloweralkyl, carboalkoxyloweralkyl, loweralkanoyl, loweralkanesulfonyl, arylsulfonyl, sodium sulfo loweralkyl, sulfo loweralkyl, loweralkenyl, loweralkynyl, phenylloweralkyl and -hydroxyloweralkyl; $R_5$ is selected from the group consisting of hydrogen, loweralkyl, hydroxy, loweralkoxy, haloloweralkyl, phenyl, carboxyphenyl, chlorophenyl, sodium sulfophenyl, pyridyl, pyridyl loweralkyl, (mono- and polyhydroxy)lower alkyl, ω-loweralkoxyloweralkyl, ω-di(loweralkyl)aminoloweralkyl, ω-piperidinoloweralkyl, ω-pyrrolidinohydroxylower alkyl, amino, loweralkanoylamino, loweralkanesulfonylamino, N-piperidyl, arylsulfonylamino, and 4-loweralkyl-1-piperazino; $R_4$ and $R_5$ taken together with the associated nitrogen is selected from the group consisting of pyrrolidino, piperidino, morpholino, hexamethyleneimino, 4-(loweralkyl)piperidino, 4-loweralkyl-1-piperazino, 4-phenylpiperazino, 3-pyrrolinyl, $\Delta^3$-piperidino, 4-(carboethoxy or carboxy)-3-thiazolidinyl and 4-(carboethoxy)-3-oxazolidinyl; $R_6$ and $R_7$ are the same or different and are selected from the group consisting of loweralkyl, (mono- and polyhydroxy)loweralkyl, carboxyloweralkyl, sulfo loweralkyl, sodium sulfo loweralkyl, and, when taken together, loweralkylene; R is selected from the group consisting of hydrogen, or a group convertible in vivo thereinto, such as methyl; carboxymethyl, acetyl, succinyl, 1-(sodium sulfo)loweralkyl, 1-(sodium sulfo)polyhydroxyalkyl and 1,3-bis-(sodium sulfo)-aralkyl; and wherein $R_1$ is a:

Formula (I-A): $C_2$ to $C_{21}$ E- or Z-alkenyl group unsubstituted or substituted with at least one lower alkyl group;

Formula (I-B): $C_2$ to $C_{20}$ alkynyl group unsubstituted or substituted with at least one methyl or ethyl group;

Formula (I-C): $C_4$ to $C_{20}$ alkyl group containing at least 2 non-cumulative double bonds, said group being unsubstituted or substituted with at least one methyl or ethyl group;

Formula (I-D): $C_3$ to $C_{12}$ allenyl group unsubstituted or substituted with at least one methyl or ethyl group;

Formula (I-E): vinyl or $C_3$ to $C_8$ E- or Z-alkenyl group said vinyl or alkenyl group being unsubstituted or substituted with at least one methyl group, and in this Formula I-E, $R_2$ is a vinyl or $C_3$ to $C_8$ E- or Z-alkenyl group unsubstituted or substituted with at least one methyl group;

Formula (I-F): allyl or $C_4$ to $C_8$ E- or Z-alkenyl group said allyl or alkenyl group being substituted with at least one exo-(methylene, ethylidene, or isopropylidene), and either further unsubstituted or substituted with at least one methyl group;

Formula (I-G): vinyl or $C_3$ to $C_8$ E- or Z-alkenyl group substituted between the nitrogen and the double bond with at least one loweralkenyl said vinyl or alkenyl group being unsubstituted or substituted with at least one methyl group;

Formula (I-H): vinyl $C_3$ to $C_8$ E- or Z-alkenyl group said vinyl or alkenyl group being unsubstituted or substituted with at least one methyl and in this case, $R_2$ is a $C_2$ to $C_9$ alkynyl group unsubstituted or substituted with at least one methyl group;

Formula (I-I): $C_4$ to $C_{20}$ alkyl group containing at least one carbon-carbon double bond and at least one carbon-carbon triple bond said group being unsubstituted or substituted with at least one loweralkyl group;

or wherein R' is a:

Formula (I-J): group of the formula

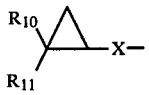

wherein $R_{11}$ is hydrogen or a $C_1$ to $C_{15}$ alkyl group unsubstituted or substituted with at least one methyl group, $R_{10}$ is hydrogen or methyl and X is a bond or a $C_1$ to $C_{15}$ branched or unbranched alkylene group unsubstituted or substituted with at least one methyl group;

and the pharmaceutically acceptable non-toxic acid addition and cationic salts thereof.

The loweralkyl, loweralkenyl, loweralkynyl, loweralkoxy, loweralkanoyl, and loweralkanesulfonyl groups referred to herein contain 1 to 6 carbon atoms and are optionally unbranched or branched. The polyhydroxy and polycarboxy groups referred to above contain 2 to 4 hydroxy or carboxy groups, respectively.

Preferred compounds of Formula I, including preferred compounds of Formulas I-A through I-J are described below.

Preferred compounds of Formula I are those wherein Z is:

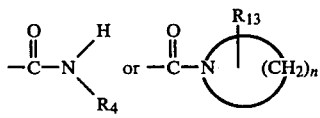

wherein $R_4$ is a loweralkyl group substituted with at least one hydroxyl group, allyl, propargyl, 2-sulfoethyl, —$(CH_2)_m$—$COOR_9$ wherein m is 2–4 and $R_9$ is hydrogen or a loweralkyl group,

wherein $R_{12}$ is a loweralkyl or aryl group, —$SO_2R_{12}$,

or a —$NHSO_2$—$R_{12}$ group; n is one of the integers 4, 5 and 6 and $R_{13}$ is hydrogen or at least one methyl group.

Also preferred are compounds of Formula I wherein Z is the moiety

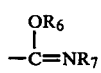

wherein $R_6$ and $R_7$ are as previously defined.

Additionally preferred compounds of Formula I are those where D is hydroxy; a loweralkoxy group unsubstituted or substituted with one or more carboxyl, hydroxyl, diloweralkylamino or polymethyleneimino (ring size 5–8) groups; a benzyloxy or phenoxy group which is unsubstituted or substituted with at least one halogen or carboxyl group; or 3-pyridyloxy.

Preferred compounds of Formula I are those wherein R is hydrogen, $R_2$ and $R_3$ are hydrogen or methyl.

Preferred compounds of Formula I-A are those where $R_1$ is a vinyl or $C_3$ to $C_{21}$ E- or Z-alkenyl group said vinyl or alkenyl group being unsubstituted or substituted with at least one methyl group; the most preferred compounds of Formula I-A are those wherein $R_1$ is a $C_7$ to $C_{15}$ E- or Z-alkenyl group; and the most preferred of these are those in which R, $R_2$ and $R_3$ are hydrogen.

Preferred compounds of Formula I-B are those wherein $R_2$ and $R_3$ are methyl; even more preferred compounds of Formula I-B are those wherein $R_1$ is $C_2$ to $C_{18}$ alkynyl and most preferred are those wherein $R_1$ is $C_7$ to $C_{18}$ alkynyl; and the most preferred of these are those wherein R, $R_2$ and $R_3$ are hydrogen.

Preferred compounds of Formula I-C are those wherein $R_2$ and $R_3$ are hydrogen or a loweralkyl group and those compounds of Formula I-C wherein $R_1$ is $C_4$ to $C_{18}$ alkyl group containing at least two non-cumulative double bonds; and most preferred of these are those wherein R, $R_2$ and $R_3$ are hydrogen.

Preferred compounds of Formula I-D are those wherein $R_2$ is methyl; more preferred compounds are those of Formula I-D wherein $R_1$ is a $C_3$ to $C_{12}$ allenyl group and the other groups are as defined above; and the most preferred of these are those wherein R, $R_2$ and $R_3$ are hydrogen.

Preferred compounds of Formula I-E are those wherein $R_1$ is a $C_2$ or $C_3$ alkenyl group; and the most preferred of these are those wherein R, $R_2$ and $R_3$ are hydrogen.

Particularly preferred compounds of Formula I-F are those wherein R, $R_2$ and $R_3$ are hydrogen.

Particularly preferred compounds of Formula I-G are those wherein R, $R_2$ and $R_3$ are hydrogen.

Particularly preferred compounds of Formula I-H are those where R, $R_2$ and $R_3$ are hydrogen; more preferred compounds are those where $R_1$ is a loweralkenyl or loweralkynyl group.

Particularly preferred compounds of Formula I-I are those wherein $R_2$ and $R_3$ are the same or different and each is hydrogen or methyl. More preferred compounds of Formula I-I are those wherein $R_3$ and/or $R_2$ is hydrogen; and other preferred compounds of Formula I-I are those wherein $R_1$ is a $C_4$ to $C_{13}$ alkyl group containing at least one carbon-carbon double bond and at least one carbon-carbon triple bond. Most preferred compounds of Formula I-I are those wherein $R_1$ is a $C_6$ to $C_{18}$ alkyl group containing at least one carbon-carbon double bond and at least one carbon-carbon triple bond.

Particularly preferred compounds of Formula I-J are those wherein $R_{10}$ is hydrogen. Most preferred compounds of Formula I-J are those wherein R, and $R_{10}$ are hydrogen.

Suitable keto-acids and keto-esters contemplated by the present invention are those in which the group D is selected from the group consisting of carboxymethyl; carboxyethyl; 2-carboethoxy-2-propyl; dicarboethoxymethyl; carboethoxyvinyl and the like. Suitable alkanoic, alkenoic and alkynoic acids and esters are those in which the radical Z is selected from the group consisting of 4-carboxybutyl; 2-carboethoxyethyl; 2-carboxyvinyl, 2-carboethoxyethynyl, and the like.

The invention also pertains to novel compositions of matter useful as antiatherosclerotic agents and to methods of ameliorating atherosclerosis by counteracting hyperlipemia and arterial plaque formation in mammals therewith; the active ingredients of said compositions of matter being the novel 2- or 3-[(unsaturated or cyclopropylated alkyl)amino]phenyl compounds of the present invention. These compounds may be utilized either as such or in the form of a pharmaceutically acceptable salt with an organic or inorganic acid or base. The invention also contemplates a method for lowering serum lipids and for ameliorating atherosclerosis in mammals by the administration of said compounds.

BACKGROUND OF THE INVENTION

Considerable effort has been directed in recent years to obtain substances useful in counteracting the consequences of hyperlipidemia, a condition involving elevated cholesterol, phospholipid and/or triglyceride levels in the blood, and of hyperlipoproteinemia, involving an imbalance of the lipo-proteins. The most serious condition associated with hyperlipidemia and hyperlipoproteinemia is atherosclerosis, a form of arteriosclerosis characterized by lipid accumulation and thickening of the walls of both medium-sized and large arteries such as the aorta. Their walls are thereby weakened and the elasticity and effective internal size of the arteries decreased. Atherosclerosis, the most common cause of coronary artery disease, is of great medical importance since it tends to occlude those arteries supplying blood to the heart muscles and brain, thereby producing permanent damage to these organs. Such damage may lead to ischemic heart disease, congestive heart failure, lifethreatening arrhythmias, senility, or stroke. Involvement of leg arteries may lead to gangrene and loss of the limb. It has been known for more than 100 years that cholesterol is a major component of atherosclerotic lesions or plaques. Investigators have been trying to determine the role of cholesterol in lesion initiation and development and also, more importantly, whether lesion formation can be prevented or reversed and enlargement of lesions be slowed or stopped. The earliest lesions are now known to be fatty streaks, largely of cholesterol, which often progress in stages to plaques containing cellular, fibrous and calcified material in addition to the lipids.

The evidence that hyperlipidemia is one of the factors involved in coronary heart disease is very impressive. A most important study carried out in Framingham, Mass. (Gordon and Verter, 1969) in over 5,000 persons for more than 12 years established a correlation between high concentrations of blood cholesterol and increased risk of heart attack. Although the causes of coronary artery disease are multiple, one of the most constant factors has been the elevated concentration of lipids in the blood plasma. A combined elevation of cholesterol and triglycerides have been shown (Carlson and Bottiger, 1972) to carry the highest risk of coronary heart disease. The majority of patients with ischemic heart disease or peripheral vascular disease were found to have hyperlipoproteinemia, involving very low-density and/or low-density lipoproteins (Lewis et al. 1974).

The reason for most treatment of hyperlipidemia or hyperlipoproteinemia is for arresting, reversing or preventing atherosclerosis. In the past, attempts have been made to lower the levels of cholesterol, phospholipids, and triglycerides in the blood by the oral feeding of various substances which have been generally referred to in the art as hypolipidemic agents or hypocholesteremic adjuvants. Typical of such substances are lecithin, pectin, cottonseed oil, and the mucilaginous substances listed in U.S. Pat. No. 3,148,114. In addition, several synthetic hypolipidemic agents are now available, namely, clofibrate, D-thyroxine, cholestyramine, and nicotinic acid [Levy and Frederickson, Postgraduate Medicine 47, 130 (1970)]. Clofibrate has the undesirable side-effect of causing hypertrophy of the liver in some patients.

The development of agents capable of reducing elevated blood lipids and of favorably altering blood-lipoprotein patterns is considered by medical authorities to be extremely important for the treatment and prevention of atherosclerosis.

Related compounds are the subject of my copending applications Ser. No. 884,673, filed Mar. 8, 1978 now U.S. Pat. No. 4,230,878 and Ser. No. 8,641, filed Feb. 1, 1979, now U.S. Pat. No. 4,281,019.

DETAILED DESCRIPTION OF THE INVENTION

The compounds of this invention are new and novel 2- or 3-[(unsaturated or cyclopropylated alkyl)amino]phenyl compounds and derivatives of Formula I (including Formulas I-A to I-J) which have useful biological and pharmacological properties. No hypolipidemic activity has been reported in the literature for these compounds and they are different in structure from other hypolipidemic agents. The compounds of this invention lower serum-lipid concentrations and also minimize atheroma formation in the aorta. These substances also provide the oral administration required for hypolipidemic agents, which patients usually take for many years. The novel compounds of this invention are adequately absorbed from the gastrointestinal tract.

We have now found that the compounds of the present invention can safely and effectively lower both serum sterols and triglycerides in warm-blooded mammals. Such actions on serum-lipid components are considered to be very useful in the treatment of atherosclerosis, especially in contrast to available drugs whose action is much more limited. For some time it has been considered desirable to lower serum-lipid levels and to correct lipoprotein imbalance in mammals as a preventive measure against atherosclerosis. The compounds of the present invention do not act by blocking late stages of cholesterol biosynthesis and thus do not produce accumulation of intermediates such as desmosterol, as equally undesirable as cholesterol itself. Compounds with the combination of therapeutically favorable characteristics possessed by those of the present invention can be safely administered to warm-blooded mammals for the treatment of hyperlipidemic and atherosclerotic states found in patients with or prone to heart attacks, to peripheral or cerebral vascular disease, and to stroke.

The novel compounds of the present invention are, in general, white crystalline solids having characteristic melting points and absorption spectra. They are soluble in organic solvents such as lower alkanol, chloroform, benzene, dimethylformamide, and the like, but are generally not very soluble in water. The novel compounds of the present invention, which are organic bases may be converted to their non-toxic acid-addition or cationic salts with a variety of pharmaceutically acceptable organic and inorganic salt-forming reagents. Thus, acid-addition salts may be formed by admixture of the organic free base in a neutral solvent with one or two equivalents of an acid such as sulfuric, phosphoric, hydrochloric, hydrobromic, trifluoroacetic, citric, ascorbic, and the like. The compounds which contain acidic groups form pharmaceutically acceptable cationic salts with organic or inorganic bases such as the alkali metal hydroxides, the alkaline earth metal hydroxides, and the like. The sodium or potassium salts which are formed in solution in the course of hydrolysis of their esters can be isolated as the solid alkali metal salts by cooling. Where it is desirable to purify a compound in the form of the acid, the salt is conveniently formed by treating its solution with exactly one equivalent of base and evaporation or lyophilization. Alkaline earth salts are prepared similarly, often using their acetate salts as a conveniently soluble form. Organic base salts such as those of N-methylglucamine are prepared by dissolving equimolar amounts of the acid and the base in hot ethanol or aqueous alcohols and cooling to crystallization.

The 2- or 3-[(unsaturated or cyclopropylated alkyl)amino]phenyl compounds of this invention are prepared by reaction of the corresponding 2- or 3-aminophenyl compounds with suitable alkylating agents, such as (unsaturated or cyclopropylated alkyl) halides, sulfates, tosylates, mesylates or trifliuoromethylsulfonates, with or without a solvent at 25°–150° C. Suitable solvents are lower alkanols, chloroform, N,N-dimethylformamide, N,N-dimethylacetamide, diglyme, dimethylsulfoxide, acetonitrile, toluene, benzene, hexamethylphosphoramide and like solvents. The reaction may be carried out with 2 equivalents of the unsubstituted amine compound or with only one equivalent and one equivalent of an unreactive organic base such as diisopropylethylamine or an alkali carbonate or bicarbonate, or with a catalytic amount of copper powder when an appropriate halide is used as the alkylating agent.

The N-acetyl-2- or 3-(substituted-amino)phenyl compounds are prepared by reaction of a corresponding 2- or 3-(acetylamino)phenyl compound with an appropriate (unsaturated or cyclopropylated alkyl) halide in the presence of an equivalent of sodium hydride in an inert solvent such as N,N-dimethylformamide, N,N-dimethylacetamide or diglyme at 50°–150° C. The N-acetyl compounds are readily hydrolyzed to the acids in boiling aqueous ethanolic dilute alkali or acid.

Alternative methods of preparation are by reductive alkylation of a 2- or 3-aminophenyl compound which may also be generated in situ by reduction of 2- or 3-amino precursors such as a 2- or 3-nitro group and the like, or by a borohydride reduction of a 2- or 3-(acylamino)phenyl compound. For example, a carbonylalkene such as an unsaturated ketone or aldehyde and ethyl 2-aminophenylacetate or methyl 2-aminobenzoate and the like are reduced under 1-10 atmospheres of hydrogen using a suitable metal catalyst or with a metal hydride such as sodium borohydride forming the corresponding phenylacetic or benzoic acid and the like. Diborane reduction of 2- or 3-(cyclopropylalkanoylamino)phenyl compounds such as ethyl 2- or 3-(11-cyclohexylundecanoylamino)phenylacetate at room temperature or above for 1-6 hours yields the corresponding 2- or 3-(cyclopropylalkylamino)phenyl compounds such as ethyl 3-(11-cyclopropylundecylamino)phenylacetate. The 2- or 3-(cyclopropylalkanoylamino)phenyl compounds used in these reductions are prepared by acylation of the appropriate 2- or 3-aminophenyl compounds with suitable acylating agents, such as cyclopropylalkanoyl halides. To prepare the 2- or 3-(substituted-amino)phenyl alkenoic and alkynoic acids it is advantageous to form the corresponding alkylchloromide from the 2- or 3-(acylamino)phenyl compounds using phosphorous oxychloride and base, and then reduce the alkylchloromide moiety to an alkylamino group with sodium borohydride.

The 2- or 3-(substituted amino)phenyl compounds of this invention are often prepared from the corresponding 2- or 3-aminophenyl compounds by the sequence involving esterification of any carboxyl group present with ethanol or methanol in the presence of boron trifluoride etherate, followed by alkylation of the amino function as described above. The free acids are then liberated by hydrolysis of the ester with aqueous alcoholic sodium hydroxide at 80° C. for 2-10 hours followed by acidification. The acids obtained by this procedure may be converted to the corresponding cationic salts. For example, the sodium salt may be prepared by reaction of the benzoic acid with sodium hydroxide in a mixture of ethanol and water. Alternatively, the free acids may be prepared by hydrolysis of the corresponding nitriles or various amides, imidates or oxazolines.

The 2- or 3-[(unsaturated or cyclopropylated alkyl)amino]phenyl compounds and derivatives are prepared by deacylation of the corresponding 2- or 3-[(N-trifluoroacetyl)-(unsaturated or cyclopropylated alkyl)amino]phenyl compounds by reacting with an alkali hydroxide such as sodium or potassium hydroxide in a lower alkanol, water or an aqueous lower alkanol at 5° C. to 50° C. Alternatively, these compounds may be prepared by deacylation of the 2- or 3-(N-carbo-t-butoxyalkenylamino)phenyl compounds with mineral acids such as hydrochloric or hydrobromic acid, preferably in glacial acetic acid at 0° C. to 50° C. Also, they are prepared by removal of the carbobenzyloxy protecting group from the anilino nitrogen atom by means of mild catalytic hydrogenation or by treatment with a mineral acid such as hydrobromic acid in glacial acetic acid.

With certain kinds of substrates for amide formation, it is necessary to form the alkali metal or strong organic base salts of these substrates in order to react them with the various aforementioned acylating forms of the 2- or 3-[(unsaturated or cyclopropylated alkyl)amino]benzoic acids. The aminoalkanecarboxylic and aminoalkanesulfonic acids are zwitterionic and must be converted to their cationic salts, suitably in situ. They may also be used in the form of their esters and then hydrolyzed after amide formation. Certain substrates, which are neutral like the carboxamides or slightly acidic like the alkane or arene sulfonamides, are converted to reactive salts by reaction with sodium hydride or other basic reagents.

Alternatively the free acids may be prepared by hydrolysis of the corresponding nitriles or various amides, imidates or oxazolines. The carboxylic acid moiety may also be generated by oxidation of the corresponding aldehydes, acetophenones, benzyl alcohols, or toluenes, most often with the use of an amine-protecting group such as trifluoroacetyl or t-butyloxycarbonyl.

The imidates of the present invention are preferably prepared either by addition of hydroxy compounds to the corresponding nitriles or by alkylation of the corresponding amides, suitably bearing a protecting group on the aromatic amino nitrogen atom in many cases. The addition of alcohols and other hydroxy compounds is carried out under acid catalysis without additional solvent, if possible. Alkylation of the protonated substituted aminoamide may be carried out or the aforementioned amino protecting groups can be employed. In some cases, simultaneous O-alkylation of the amide and N-alkylation of the aromatic amino moiety can be used to obtain a desired imidate. Intramolecular formation of imidates results from 2-haloethyl and 3-halopropyl amides as well as from 2-hydroxyethyl and 3-hydroxypropyl amides when treated with a condensing agent.

Certain derivatives

of the aminophenyl nitrogen atom are useful for providing greater solubility, more uniform and reliable intestinal absorption, and for a certain degree of modification of the pharmacology of the compounds of the present invention. Some of these derivatives can be converted to the corresponding N-H forms by the acidity of the stomach or the alkalinity of the small intestine. Others are converted by metabolic processes. The methyl and carboxymethyl derivatives and the like are prepared by the alkylation, reductive alkylation, and acylamino reduction methods above. Derivatives such as the acetyl and succinyl compounds may be prepared using acetyl chloride, acetic anhydride, succinic anhydride, etc., in the presence of pyridine, triethylamine or the like at temperatures moderate enough to avoid acylation of the amide moiety. The 1-(sodium sulfo)alkyl derivatives are obtained by reaction of the 2- or 3-[(unsaturated or cyclopropylated alkyl)amino]phenyl compound with sodium bisulfite and an aliphatic aldehyde, a polyhydroxyaldehyde such as glyceraldehyde or glucose, or cinnamaldehyde in a mixed organic aqueous medium. In the case of cinnamaldehyde, the di-sulfonate salts result from addition of the bisulfite to the carbon-nitrogen double bond of the anil intermediate as well as to the carbon-carbon double bond of cinnamaldehyde itself.

In certain cases, the unsaturation is introduced at a late stage of the preparation, of the 2- or 3-(unsaturated alkylamino)phenyl compounds. For example, a 2- or 3-(ω-haloalkylamino)phenyl compound is dehydrohalogenated to the corresponding olefinic compound or, alternatively, it is converted to a Wittig trialkylphosphonium reagent and reacted with an aldehyde to yield a product with an internal double bond. This ω-halo substrate can also be reacted with an alkylacetylene sodium or lithium salt to form the corresponding 2- or 3-alkynylamino derivatives.

The carboxaldehydes of this invention may be prepared by several methods among which is alkylation of the corresponding acetals as described above followed by hydrolysis of the resulting 2- or 3-(substituted-amino)phenyl compound to the desired aldehyde. Aldehydes may also be prepared by reduction of the appropriate nitriles. For example, treatment of 2-(hex-3-enylamino)hydrocinnamonitrile with stannic chloride and anhydrous hydrogen chloride gas, followed by hydrolysis in hot water provides 2-(hex-3-enylamino)-hydrocinnamaldehyde. These reductions are also conveniently carried out with hydrides such as diisobutylaluminum hydride.

The α-substituted 2- or 3-(substituted-amino)acetophenones of the invention are prepared by reaction of a derivative of the appropriate benzoic acid, such as 2- or 3-(4-pentadecenylamino)phenylacetyl chloride hydrochloride, with two or more equivalents of the reactive salt of an acidic methylene compound, for example the sodium salt of diethyl malonate. Other benzoic acid derivatives are also suitable for this reaction, such as an N-trifluoroacetyl or N-tert-butyloxycarbonyl acid chloride, or a methyl ester of the acid. In some cases the final step in the preparation of the α-substituted 2- or 3-(substituted-amino)acetophenone is the removal of the nitrogen-protecting group. In other cases, hydrolysis of one or more of the ester groups in the acylation product affords an unstable polycarboxylic acid which undergoes decarboxylation to allow the preparation of another acetophenone derivative. For example, the reaction of tert-butyl ethyl [3-(4-pentadecenylamino)benzoyl]malonate with trifluoroacetic acid affords ethyl [3-(4-pentadecenylamino)benzoyl]acetate. In other cases, hydrolysis of one or more of the ester groups allows the preparation of the corresponding acid derivative. For example, the hydrolysis of ethyl [2-(hept-3-enylamino)benzoyl]acetate yields 2-(hept-3-enylamino)benzoylacetic acid.

An alternative procedure for preparing certain 2- or 3-(substituted-amino)acetophenones is alkylation of the corresponding 2- or 3-aminoacetophenone by the methods above. For Example, alkylation of methyl 3-(3-aminobenzoyl)propionate with undec-10-enyl bromide yields methyl 3-[3-(undec-10-enylamino)benzoyl]propionate. The related carboxylic acids are then obtained by hydrolysis. Certain of these acids are particularly useful for the preparation of 2- or 3-(substituted amino)-phenylalkanoic acids by reduction. For example, the Clemmensen or Wolff-Kishner reduction of 3-[3-(hex-3-enylamino)benzoyl]propionic acid yields 4-[3-(hex-3-enylamino)phenyl]butyric acid.

The 2- or 3-(substituted-amino)phenylalkenoic acids may be prepared by condensation of the appropriate aldehydes or by dehydration of the corresponding substituted phenylhydroxyalkanoic acids. For example, ethyl 5-[3-(undec-10-enylamino)phenyl]-2,4-pentadienoate is obtained by the Wittig reaction of 3-(undec-10-enylamino)benzaldehyde with the Wittig reagent, triethyl 4-phosphonocrotonate. Alternatively, these alkenoic acids are obtained by heating a 2- or 3-[N,N-disubstituted-amino]benzaldehyde and the like with the sodium salt of the carbanion of ethyl acetate or with a mixture of ethyl acetate, acetic anhydride and potassium acetate. The second method is illustrated by dehydration of ethyl 3-[2-(undec-10-enylamino)-phenyl]-3-hydroxypropionate to the corresponding cinnamate.

The acetylenic analogs are prepared by dehydrobromination of the side-chain vic-dibrominated alkanoic acid. For example, dehydrobromination of ethyl 3-[3-(allylamino)phenyl]-2,3-dibromopropionate, its isomers or N-acyl analogs or of ethyl 3-[3-(allylamino)phenyl]-3-bromoacrylate yields ethyl 3-(allylamino)phenylpropiolate. The acetylenic acids are also formed from (2- or 3-substituted-amino)phenylacetylene metal salts by carboxylation with carbon dioxide. The 2- or 3-(substituted-amino)phenylacetylenes are also prepared by N-acylating with t-butyl azidoformate followed by conversion to the lithium acetylide salt and the subsequent reaction of the lithium salt with boron trifluoride etherate in tetrahydrofuran at −20° C. to form tris-[(2- or 3-substituted-amino)phenylethynyl]boranes. The tetrahydrofuran solution of the borane is in turn reacted with ethyl diazoacetate, followed by water to yield ethyl 4-[(2- or 3-substituted-amino)phenyl]butynoate.

The 2- or 3-(substituted-amino)phenylalkanoic acids, or esters are also prepared by catalytic reduction at 1 to 10 atmospheres of hydrogen of the corresponding alkenoic or alkynoic acid derivatives. The 2- or 3-(substituted-amino)phenylalkenoic acids and derivatives are prepared by Friedel-Crafts acylation of the N-acyl-N-alkylanilines with the appropriate dicarboxylic acid anhydride or half acid chloride. The 2- or 3-(substituted-amino)benzoylalkanoic acids or esters, obtained by this and by other syntheses, may be converted to the corresponding 2- or 3-(substituted-amino)phenylalkanoic acids by reduction with (a) hydrazine and alkali in diethylene glycol at 140° for 3 hours, (b) zinc amalgam and ethanolic hydrochloric acid at 60° for 5 hours, (c) red phosphorus and hydriodic acid, or (d) ketalization with 1,2-ethanedithiol followed by Raney nickel desulfurization. The amides of these 2- or 3-(substitutedamino)phenylalkanoic acids are prepared by heating the corresponding 2- or 3-(substituted-amino)-phenylalkyl ketones with aqueous alcoholic ammonium polysulfide followed by hydrolysis to yield the acids with the same number of carbon atoms as the ketone. These acids are also prepared by reacting a 2- or 3-(N-butyloxycarbonyl-N-substituted-amino)phenylmagnesium halide with 2-(3-halopropyl)-2-oxazolines, followed by mild acid removal of 2-oxazolinyl and t-butoxycarbonyl protecting groups. Similarly, the above Grignard reagent can be reacted with 3-bromotriethylorthopropionate in the presence of dilithium-tetrachlorocuprate to yield the desired acids after removal of the protecting groups from the amino and carboxyl groups.

The novel 2- or 3-(substituted-amino)phenyl compounds of the present invention are not only potent hypolipidemic agents but also prevent or diminish the formation or enlargement of arterial plaques in mammals when administered in amounts ranging from about one mg. to about 250 mg. per kilogram of body weight per day. A preferred dosage regimen for optimum results would be from about 5 mg. to about 100 mg. per kilogram of body weight per day, and such dosage units are employed that a total of from about 0.35 grams to about 7.0 grams of the active compound, for a subject of about 70 kg. of body weight, are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compound may be administered in a convenient manner by the oral route. The compounds of the present invention exert a more powerful hypocholesteremic and antiatherosclerotic effect than the aforementioned adjuvants and synthetic medicaments. It is not known how these novel compounds operate in the blood serum and no theory of why these compounds so operate is advanced. It is not intended that the present invention should be limited to any particular mechanism of action of lowering serum lipids or of ameliorating atherosclerosis, or be limited to compounds acting by only one mechanism.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active ingredient in such therapeutically useful compositions is such that a suitable dosage will be obtained. Preferred compositions or preparations according to the present invention are prepared so that an oral dosage-unit form contains between about 50 and 250 milligrams of active compound.

The tablets, troches, pills, capsules and the like may also contain the following: a binder such as gum tragacanth, acacia, corn starch or gelatin; excipients such as dicalcium phosphate, a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage-unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propyl parabens as preservatives, a dye, and flavoring such as cherry or orange flavor. Of course, any material used in preparing any dosage-unit form should be pharmaceutically pure and substantially non-toxic in the amounts employed. In addition, the active ingredients may be incorporated into sustained-release preparations and formulations.

The invention will be described in greater detail in conjunction with the following specific Examples.

EXAMPLE 1

Preparation of 3-(allylamino)phenylacetic acid (Method A)

To a solution of 18.2 g. of ethyl 3-aminophenylacetate in 100 ml. of dimethylformamide is added a solution of 4.7 ml. of allyl bromide in 60 ml. of dimethylformamide. The solution is heated at 60° C. for 5 hours and then cooled and partitioned between diethyl ether and water. The combined ether phases are washed with water, dried over magnesium sulfate, and concentrated in vacuo to provide 16.5 g. of a semi-solid. A portion (6 g.) is absorbed onto 30 g. of silica gel and chromatographed on 475 g. of silica gel to provide ester.

A mixture of the ester, 22.0 g. of potassium hydroxide and 200 ml. of ethanol-water (8:1) is stirred under reflux for 6 hours. Concentrated hydrochloric acid (about 80 ml.) is added to the warm mixture and cooling and dilution with water affords a white solid which is collected by filtration and recrystallized from ethanol to yield the product as a white solid.

EXAMPLE 2

Preparation of 3-(1-pentadeca-4,14-dienylamino)benzoic acid (Method B)

To a solution of 4,14-pentadecadien-1-ol (15.0 g.) and triethylamine (14 ml.) in dry methylene chloride (320 ml.) at −8° C. is added methanesulfonylchloride (5.73 ml.), dropwise. The reaction mixture is stirred at −10° C. for 30 minutes and then diluted with methylene chloride, extracted with ice-water (250 ml.); followed by cold 10% hydrochloric acid (200 m.); cold saturated sodium bicarbonate (200 ml.) and cold brine (200 ml.). The organic phase is dried over magnesium sulfate and the solvent removed in vacuo to provide the crude mesylate.

A solution of 18.1 g. of the above mesylate and 19.8 g. of ethyl 3-aminobenzoate in hexamethylphosphoramide is heated at 120° C. for 20 hours. After cooling, the reaction mixture is diluted with 30 ml. of ethanol:water (1:1) (30 ml.) and chilled. More ethanol is added and the solid material is collected. This solid is recrystallized twice from ethanol to provide the ester.

A mixture of the ester, 22.0 g. of potassium hydroxide and 200 ml. of ethanol-water (8:1) is stirred under reflux for 6 hours. Concentrated hydrochloric acid (about 80 ml.) is added to the warm mixture and cooling and dilution with water affords a white solid which is collected by filtration and recrystallized from ethanol to yield the product as a white solid.

EXAMPLES 3–317

Treatment of the indicated halide or carbinol starting material set forth in Table I below by the indicated method is productive of the product listed in the table. Reference B in Tables I and II is J. Med. Chem. 11, 1190 (1968).

TABLE I

| Example | Starting Material | Method | Product |
|---|---|---|---|
| 3 | E-4-tetradecenol | B | 2-(E-1-tetradec-4-enylamino)-phenylacetic acid |
| 4 | Z-9-octadecen-1-ol | B | 3-(Z-1-octadec-9-enylamino)benzoic acid |
| 5 | E-4-pentadecen-1-ol | B | 2-(E-1-pentadec-4-enylamino)phenyl-acetic acid |
| 6 | 3-chloro-2,4,4-trimethyl-1-pentene Chem. Abst. 72, 111081h | A | 3-[3-(2,4,4-trimethyl)-penty-1-enylamino]benzoic acid |
| 7 | 3-bromo-3-isopropyl-4-methyl-1-pentene Chem. Abst. 54, 4355a | A | 2-[3-(3-isopropyl-4-methyl)pent-1-enyl-amino]phenyl-acetic acid |
| 8 | 4-bromo-2-heptene Chem. Abst. 70, 67482x | A | 3-(4-hept-2-enyl-amino)benzoic acid |
| 9 | 4-bromo-2,4-dimethyl-2-hexene | A | 2-[4-(2,4-dimethyl-hex-2-enyl)amino]-phenylacetic acid |
| 10 | 5-chloro-3,5-dimethyl-3-heptene Chem. Abst. 54, 1256e | A | 3-[5-(3,5-dimethyl-hept-3-enyl)amino]-benzoic acid |
| 11 | z-1-hydroxy-2-hexadecene Ref. B | B | 2-(Z-1-hexadec-2-enylamino)phenyl-acetic acid |
| 12 | E-1-hydroxy-2-hexadecene Ref. B | B | 3-(E-1-hexadec-2-enylamino)phenyl-acetic acid |
| 13 | 1-bromo-4-methyl-3-heptene Chem. Abst. 71, 102020q | A | 2-[1-(4-methylhept-3-enyl)amino]benzoic acid |
| 14 | 1-bromo-4-methyl-3-nonene Chem. Abst. 71, 101399h | A | 3-[1-(4-methynon-3-enyl)amino]phenyl acetic acid |
| 15 | E-7-bromo-3-heptene Chem. Abst. 74, 99419f | A | 2-(1-hept-4-enyl-amino)benzoic acid |
| 16 | 1-bromo-5,9-dimethyl-4-decene Chem. Abst. 51, 8699g | A | 3-[1-(5,9-dimethyl-dec-4-enyl)amino]-phenylacetic acid |
| 17 | 1-methanesulfonyl-oxy-4-tetradecene Ref. B. | B | 2-(1-tetradec-4-enylamino)phenyl-acetic acid |
| 18 | 1-methanesulfonyl-oxy-4-hexadecene Ref. B. | B | 3-(1-hexadec-4-enylamino)benzoic acid |
| 19 | 6-bromo-1-hexene Chem. Abst. 66, 2142j | A | 2-(1-hex-5-enyl-amino)phenylacetic acid |
| 20 | 6-bromo-2-methyl-1-hexene Chem. Abst. 75, 109624f | A | 3-[1-(5-methylhex-5-enyl)amino]benzoic acid |
| 21 | 6-chloro-1-heptene Chem. Abst. 72, 31877g | A | 2-(2-hept-6-enyl-amino)phenylacetic acid |
| 22 | 6-bromo-2-methyl-2-heptene Chem. Abst. 54, 13166f | A | 3-[2-(2,6-dimethyl-hept-5-enyl)amino]-benzoic acid |
| 23 | 7-chloro-2-octene Chem. Abst. 75, 129245m | A | 2-(2-oct-6-enyl-amino)phenylacetic acid |
| 24 | E-1-chloro-4-nonene Chem. Abst. 67, 32294g | A | 2-(E-1-non-5-enyl-amino)benzoic acid |
| 25 | 7-bromo-1-heptene | A | 3-(1-hept-6-enyl-amino)phenylacetic acid |
| 26 | 7-chloro-1-octene Chem. Abst. 75, 29245m | A | 2-(2-oct-7-enyl-amino)benzoic acid |
| 27 | 6-bromo-6-methyl-1-heptene Chem. Abst. 66, 94482w | A | 3-[1-(2-methylhept-6-enyl)amino]phenyl-acetic acid |
| 28 | 6-chloro-6-methyl-1-heptene Chem. Abst. 75, 129245 | A | 2-[1-(6-methylhept-6-enyl)amino]benzoic acid |
| 29 | E-8-bromo-2-octene Chem. Abst. 74, 99419f | A | 3-(1-oct-6-enyl-amino)phenyl-acetic acid |
| 30 | 8-bromo-2,6-dimethyl-2-octene Chem. Abst. 72, 90573c | A | 2-[1-(3,7-dimethyl-oct-6-enyl)amino]-benzoic acid |
| 31 | 11-bromo-5-undecene-Chem. Abst. 67, 73101b | A | 3-(1-undec-6-enyl-amino)phenylacetic acid |
| 32 | 8-bromo-1-octene Chem. Abst. 70, 10990g | A | 2-(1-oct-7-enyl-amino)benzoic acid |
| 33 | R-8-iodo-7-methyl-1-octene Chem. Abst. 74, 12573e | A | 3-[R-(2-methyloct-7-enyl)amino]phenyl-acetic acid |
| 34 | 1-chloro-7-tetradecene Chem. Abst. 54, 22461h | A | 2-(1-tetradec-7-enylamino)benzoic acid |
| 35 | 9-chloro-1-nonene Chem. Abst. 70, 114490k | A | 3-(1-non-8-enyl-amino)phenylacetic acid |
| 36 | 1-bromo-8-heptadecene Chem. Abst. 52, 249d | A | 2-(1-heptadec-8-enylamino)benzoic acid |
| 37 | E-1-bromo-9-octadecene Chem. Abst. 70, 46779j | A | 2-(E-1-octadec-9-enylamino)phenyl-acetic acid |
| 38 | Z-1-bromo-9-octadecene Chem. Abst. | A | 3-(Z-1-octadec-9-enylamino)benzoic |

TABLE I-continued

| Example | Starting Material | Method | Product |
|---|---|---|---|
| 39 | 11-chloro-1-undecene Chem. Abst. 66, P19046d 70, 46779j | A | 2-(1-undec-10-enylamino)phenylacetic acid |
| 40 | 12-iodo-3,7,11-trimethyl 1-dodecene | A | 3-[1-(2,6,10-trimethyldodec-11-enyl)amino]benzoic acid |
| 41 | 13-bromo-1-tridecene Chem. Abst. 67, 43348v | A | 2-(1-tridec-12-enylamino)phenylacetic acid |
| 42 | 22-bromo-9-docosene Chem. Abst. 73, 44976j | A | 3-[1-(2-methylhept-6-enyl)amino]benzoic acid |
| 43 | 16-methanesulfonyloxy-1-hexadecene Ref. B. | B | 2-(1-hexadec-15-enylamino)phenylacetic acid |
| 44 | propargyl alcohol | B | 3-(1-prop-2-ynylamino)benzoic acid |
| 45 | 3-chloro-1-butyne | A | 2-(2-but-3-ynylamino)phenylacetic acid |
| 46 | 3-chloro-3-methylnonyne Chem. Abst. 55, 22090i | A | 3-[3-(3-methylnon-1-ynyl)amino]benzoic acid |
| 47 | 3-bromo-1-pentadecyne Chem. Abst. 53, 21638c | A | 2-(3-pentadec-1-ynylamino)phenylacetic acid |
| 48 | 1-octyn-3-ol Chem. Abst. 66 85410n | B | 3-(3-oct-1-ynylamino)benzoic acid |
| 49 | 3,7,11,15-tetramethyl-1-hexadecyn-3-ol | B | 2-[3-(3,7,11,15-tetramethylhexadec-1-ynyl)amino]benzoic acid |
| 50 | 2-butyn-1-ol | B | 3-(1-but-2-ynylamino)phenylacetic acid |
| 51 | 4-hexyn-3-ol | B | 2-(3-hex-4-ynylamino)benzoic acid |
| 52 | 2-methyl-3-pentyn-2-ol Chem. Abst. 69, 10496e | B | 3-[2-(2-methylpent-3-ynyl)amino]phenylacetic acid |
| 53 | 2-octyn-1-ol | B | 2-(1-oct-3-ynylamino)benzoic acid |
| 54 | 4-decyn-3-ol Chem. Abst. 69, P4630s | B | 3-(3-dec-4-ynylamino)phenylacetic acid |
| 55 | 1-bromo-2-dodecyne Chem. Abst. 28, 40345 | A | 2-[1-dodec-2-ynylamino)benzoic acid |
| 56 | 1-methanesulfonyloxy-2-pentadecyne J. Med. Chem 19, 946 (1977) | B | 3-(1-pentadec-2-ynylamino)phenylacetic acid |
| 57 | 3-butyne-1-ol Chem. Abst. 66, P2319a | B | 2-(1-but-3-ynylamino)benzoic acid |
| 58 | 1-undecyn-4-ol Chem. Abst. 70, 3219j | B | 3-(4-undec-1-ynylamino)phenylacetic acid |
| 59 | 2-methyl-4-pentyn-2-ol Chem. Abst. 68, 12200g | B | 2-[2-(2-methylpent-4-ynyl)amino]benzoic acid |
| 60 | 4-pentyn-2-ol Chem. Abst. 64, 13537e | B | 3-(2-pent-4-ynylamino)phenylacetic acid |
| 61 | 3-pentyl-1-ol | B | 2-(1-hex-3-ynylamino)phenylacetic acid |
| 62 | 4-hexyn-2-ol | B | 3-(2-hex-4-ynylamino)benzoic acid |
| 63 | 2-methyl-3-pentyn-1-ol Chem. Abst. 66, 115242k | B | 2-[1-(2-methyl-3-pent-3-ynyl)amino]phenylacetic acid |
| 64 | 2-(1-propynyl)-1-heptanol Chem. Abst. 66, 115242k | B | 3-[2-(1-propynlheptyl)amino]benzoic acid |
| 65 | 2-methyl-4-nonyn-2-ol Chem. Abst. 68, 104593r | B | 2-[2-(2-methylnon-4-ynyl)amino]phenylacetic acid |
| 66 | 2-methyl-3-nonyn-1-ol Chem. Abst. 66, 115242k | B | 3-[1-(2-methylnon-3-ynyl)amino]benzoic acid |
| 67 | 3-nonyn-1-ol Chem Abst. 75 5165r | B | 2-(1-non-3-ynylamino)phenylacetic acid |
| 68 | 2-methyl-3-decyn-1-ol Chem. Abst. 66, 115242k | B | 3-[1-(2-methyldec-3-ynyl)amino]benzoic acid |
| 69 | 5-chloro-1-pentyne | A | 2-(1-pent-4-ynylamino)phenylacetic acid |
| 70 | 4-hexyn-1-ol Chem. Abst. 74, 9800w | B | 3-(1-hex-4-ynylamino)benzoic acid |
| 71 | 1-chloro-4-nonyne | A | 2-(1-non-4-ynylamino)phenylacetic acid |
| 72 | 1-chloro-4-tridecyne Chem. Abst. 32, 7426³ | A | 3-(1-pentadec-2-ynylamino)benzoic acid |
| 73 | 1-chloro-4-hexadecyne | A | 2-(1-hexadec-4-ynylamino)benzoic acid |
| 74 | 5-hexyn-1-ol Chem. Abst. 74, 9800w | B | 3-(1-hex-5-ynylamino)phenylacetic acid |
| 75 | 6-octyn-2-ol Chem. Abst. 71, 60300y | B | 2-[2-(2-methyloct-6-ynyl)amino]benzoic acid |
| 76 | 1-iodo-5-decyne Chem. Abst. 51, 12817f | A | 3-(1-dec-5-ynylamino)phenylacetic acid |
| 77 | 5-tetradecyn-1-ol Chem. Abst. 71, 12053k | B | 2-(1-tetradec-5-ynylamino)benzoic acid |
| 78 | 5-octadecyn-1-ol Chem. Abst. 72, 42686v | B | 3-(1-octadec-5-ynylamino)phenylacetic acid |
| 79 | 6-octadecyn-1-ol Chem. Abst. 72, 42686v | B | 2-(1-octadec-6-ynylamino)benzoic acid |
| 80 | 10-chloro-3-decyne Chem. Abst. 67, 108147a | A | 3-(1-dec-7-ynylamino)phenylacetic acid |
| 81 | 1-chloro-7-tetradecyne Chem. Abst. 54, 2461e | A | 2-(1-tetradec-7-ynylamino)benzoic acid |
| 82 | 7-hexadecyn-1-ol Chem. Abst. 71, 19554w | B | 3-(1-hexadec-7-ynylamino)phenylacetic acid |
| 83 | 7-octadecyn-1-ol Chem. Abst. 67, 81784w | B | 2-(1-octadec-7-ynylamino)benzoic acid |
| 84 | 8-octadecyn-1-ol Chem. Abst. 72, | B | 3-(1-octadec-8-ynylamino)phenylacetic acid |
| 85 | 9-decyn-1-ol Chem. Abst. 67, 81787s | B | 2-(1-octadec-9-ynylamino)benzoic acid |
| 86 | 10-octadecyn-1-ol Chem. Abst. 67, 81787s | B | 2-(1-octadec-10-ynylamino)phenylacetic acid |
| 87 | 4-nonyn-1-ol Chem. Abst. 67, | B | 3-(1-non-4-ynylamino)benzoic acid |
| 88 | 11-dodecyn-1-ol Chem. Abst. 68, 39015n | B | 2-(1-dodec-11-ynylamino)phenylacetic acid |
| 89 | 11-tetrdecyn-1-ol Chem. Abst. 75, 16972u | B | 3-(1-tetradec-11-ynylamino)benzoic acid |
| 90 | 11-tridecyn-1-ol Chem. Abst. 75, 1679u | B | 2-(1-tridec-11-ynylamino)phenylacetic acid |
| 91 | 16-bromo-5-hexadecyne Chem. Abst. 68, 39015n | A | 3-(1-hexadec-11-ynylamino)benzoic acid |
| 92 | 12-octadecyn-1-ol | B | 2-(1-octadec- |

TABLE I-continued

| Example | Starting Material | Method | Product |
|---|---|---|---|
| | Chem. Abst. 68, 39015n | | 12-ynylamino)phenylacetic acid |
| 93 | 12-octadecyn-1-ol Chem. Abst. 72,4286v | B | 3-(1-octadec-12-ynylamino)benzoic acid |
| 94 | 13-tetradecyn-1-ol Chem. Abst. 68, 39015n | B | 2-(1-tetradec-13-ynylamino)phenylacetic acid |
| 95 | 14-pentadecyn-1-ol Chem. Abst. 68, 39015n | B | 3-(1-pentadec-14-ynylamino)benzoic acid |
| 96 | 5,7-octadien-4-ol Chem. Abst. 72, 42686v | B | 2-(4-octa-5,7-dienylamino)phenylacetic acid |
| 97 | 4-ethyl-3,5-hexadecadien-2-ol Chem. Abst. 70 20116r | B | 3-[2-(4-ethylhexa-3-5-dienyl)amino]benzoic acid |
| 98 | 2-methyl-4,6-heptadien-3-ol Chem. Abst. 71, 112534z | B | 2-[3-(2-methylhepta-4,6-dienyl)aminophenylacetic acid |
| 99 | E-2,4,6-trimethyl-3,5-heptadien-2-ol | B | 2-[E-2(2,4,6-hepta-3,5-dienyl)amino]benzoic acid |
| 100 | 4,6-octadien-3-ol Chem. Abst. 69, 58770s | B | 3-(1-hexa-2,4-dienylamino)phenylacetic acid |
| 101 | 2,4-hexadien-1-ol Chem. Abst. 67, 81787s | B | 2-(1-hexa-2,4-dienylamino)benzoic acid |
| 102 | 6-isopropyl-7,7-dimethyl-3,5-octadien-2-ol Chem. Abst. 75, 36362g | B | 3-[2-6-isopropyl-7,7-dimethylocta-3,5-dienyl)amino]phenylacetic acid |
| 103 | 3,5,7-trimethyl-4,6-nonadien-3-ol Chem. Abst. 74, | B | 2-[3-(3,5,7-trimethylnona-4,6-dienyl)amino]benzoic acid |
| 104 | 2,6-dimethyl-3,5-octadien-2-ol Chem. Abst. 68, 114750d | B | 3-[2-(2,6-dimethylocta-3,5-dienyl)-amino]phenylacetic acid |
| 105 | E,E-6-ethyl-4,6-decadien-3-ol Chem. Abst. 73, 130585n | B | 2-[E,E-3-(6-ethyldeca-4,6-dienyl)-amino]benzoic acid |
| 106 | 5-ethyl-3,5-nonadien-2-ol | B | 3-[2-(5-ethylnona-3,5-dienyl)amino]phenylacetic acid |
| 107 | E,E-2,4-octadien-1-ol Chem. Abst. 67, 104946n | B | 2-(E,E-1-octa-2-4-dienylamino)benzoic acid |
| 108 | E,Z-2,4-nonadien-1-ol Chem. Abst. 67, 99692w | B | 3-(E,Z-1-nona-2-4-dienylamino)phenylacetic acid |
| 109 | E,E-2,4-decadien-1-ol Chem. Abst. 67, 104946n | B | 2-(E,E-1-deca-2-4-dienylamino)benzoic acid |
| 110 | E,Z-2,4-decadien-1-ol Chem. Abst. 67, 99692v | B | 3-E,Z-1-deca-2-4-dienylamino)phenylacetic acid |
| 111 | E-2,5-hexadien-1-ol Chem. Abst. 73, P55709a | B | 2-(E-1-hexa-2,5-dienylamino)phenylacetic acid |
| 112 | Z-2,5-hexadienyl-1-ol Chem. Abst. 73, PS5709a | B | 3-(Z-1-hexa-2,5-dienylamino)benzoic acid |
| 113 | E(+)-4-ethyl-2,5-dimethyl-2,5-hexadien-1-ol Chem. Abst. 71, 70152m | B | 2-(E(+)-1-(2,5-dimethylhexa-2,5-dienyl)-amino]phenylacetic acid |
| 114 | E-2,5,5-trimethyl-3,6-heptadien-1-ol Chem. Abst. 74, 52962n | B | 3-[E-2-(2,5,5-trimethylhepta-3,6-dienyl-amino]benzoic acid |
| 115 | Z-2,5,5-trimethyl-3,6-heptadien-1-ol Chem. Abst 74, 52962n | B | 2-[Z-2-(2,5,5-trimethylhepta-3,6-dienyl-amino]phenylacetic acid |
| 116 | Z,E-3,7-dimethyl-2,5-octadien-1-ol Chem. Abst. 71, 6156a | B | 3-[Z-E-1-(3,7-dimethylocta-2,5-dienyl)amino[benzoic acid |
| 117 | E-2,6-dimethyl-2,6-heptadien-1-ol Chem. Abst. 72, 32036u | B | 2-[E-1-(2,6-dimethylhept-2,6-dienyl)amino]phenylacetic acid |
| 118 | E,E-2,6-octadien-1-ol | B | 3-(E,E-1-octa-2,6-dienylamino)benzoic acid |
| 119 | E,E-2,6-dimethyl-2,6-octadien-1-ol Chem. Abst. 71, 22204n | B | 2-[E,E-1-(2,6-dimethylocta-2,6-dienyl)amino]phenylacetic acid |
| 120 | Z,E-2,6-dimethyl-octadien-1-ol Chem. Abst. 71, 22204n | B | 3-(Z,E-1-(2,6-dimethylocta-2,6-dienylamino)benzoic acid |
| 121 | E,Z-2,6-nonadien-1-ol Chem. Abst. 72, 245043 | B | 2-(E,Z-1-nona-2,6-dienylamino)phenylacetic acid |
| 122 | E,Z-3,ethyl-7-methyl-2,6-nonadien-1-ol Chem. Abst. 75, 63019g | B | 2-[E,Z-1-(3-ethyl-7-methylnona-2,6-dienyl)-amino]benzoic acid |
| 123 | 3,7,11,11-tetramethyl-2,6-dodecadien-1-ol Chem. Abst. 75, P117969n | B | 3-[1-(3,7,11,11-tetramethyldodeca-2,6-dienyl)aminophenylacetic acid |
| 124 | E,E-3,7,11-trimethyl-2,6-dodecadien-1-ol Chem. Abst. 69, 978z | B | 2-[E,E-1-(3,7,11-trimethyldodeca-2,6-dienyl)amino]benzoic acid |
| 125 | E-Z-3,7,11-trimethyl-2,6-dodecadien-1-ol Chem. Abst. 69, 978g | B | 3-(E,Z-1-(3,7,11-trimethyldodeca-2,6-dienyl)amino]phenylacetic acid |
| 126 | 2,7-octadien-1-ol Chem. Abst. 74, P41892p | B | 2-(1-octa-2,7-dienylamino)benzoic acid |
| 127 | E-3,7-dimethyl-2,7-octadien-1-ol Chem. Abst. 68, 114750d | B | 3-[E-1-(3,7-dimethylocta-2,7-dienyl)amino]phenylacetic acid |
| 128 | Z,3,7-dimethyl-2,7-octadien-1-ol Chem. Abst. 68, 114750d | B | 2-[Z-1-(3,7-dimethylocta-2,7-dienyl)amino]benzoic acid |
| 129 | 3,4,8-trimethyl-2,7-nonadien-1-ol Chem. Abst. 68, 9184c | B | 3-[1-(3,4,8-trimethylnona-2,7-dienyl)amino]phenylacetic acid |
| 130 | 3,4,8-trimethyl-2,8-nonadien-1-ol Chem. Abst. 68, 29184c | B | 2-[1-(3,4,8-trimethylnona-2,8-dienyl)amino]benzoic acid |
| 131 | 2,9-decadien-1-ol Chem. Abst. 68, 68373h | B | 3-(1-deca-2,9-dienylamino)phenylacetic acid |
| 132 | E,3,7,11-trimethyl-2,10dodecadien-1-ol Chem. Abst. 69, 978z | B | 2-[E-1-(3,7,11-trimethyldodeca-2,10-dienylamino]phenylacetic acid |
| 133 | Z-3,7,11-trimethyl-2,10-dodecadien-1-ol | B | 3-[Z-1-(3,7,11-tri methyldodeca-2,10-dienyl)amino]benzoic acid |
| 134 | E,E-4-methyl-3,5-heptadien-1-ol Chem. Abst. 66, 104730s | B | 2-[E,E-1-(4-methylhepta-3,5-dienyl)-amino]phenylacetic acid |
| 135 | E,Z-4-methyl-3,5-heptadien-1-ol Chem. Abst. 66, 104730s | B | 3-[E,Z-1-(4-methylhepta-3,5-dienyl)-amino]benzoic acid |
| 136 | Z-E-4-methyl-3,5-heptadien-1-ol Chem. Abst. 66, 104730s | B | 2-[Z,E-1-(4-methylhepta-3,5-dienyl) amino]phenylacetic acid |
| 137 | Z,Z-4-methyl-3,5- | B | 3-[Z,Z-1-(4-methyl- |

TABLE I-continued

| Example | Starting Material | Method | Product |
|---|---|---|---|
| | heptadien-1-ol Chem. Abst. 66, 104730s | | hepta-3,5-dienyl)-amino]benzoic acid |
| 138 | E-4,6-dimethyl-3,5-heptadien-1-ol Chem. Abst. 66, 104730s | B | 2-[E-1-(4,6-dimethylhepta-3,5-dienyl)amino]-phenylacetic acid |
| 139 | Z-4,6-dimethyl-3,5-heptadien-1-ol Chem. Abst. 66, 104730s | B | 3-[Z-1-(4,6-dimethylhepta-3,5-dienylamino]benzoic acid |
| 140 | E,Z-2,6-dimethyl-4,6-octadien-2-ol Chem. Abst. 68, 114750d | B | 2-[E,Z-2-(2,6-dimethylocta-4,6-dienyl)amino]phenylacetic acid |
| 141 | 1-hydroxy-3,7,11-trimethyl-2,6,10-dodecatriene | B | 3-[1-(3,7,11-trimethyldodeca-2,6,10-trienyl)amino]benzoic acid |
| 142 | 5-methyl-3,5-octadien-1-ol Chem. Abst. 69, 18519k | B | 2-[1-(5-methylocta-3,5-dienyl)amino]benzoic acid |
| 143 | E-4-methyl-3,6-heptadien-1-ol Chem. Abst. 66, 104730s | B | 3-[E-1-(4-methylhepta-3,6-dienyl)-amino]phenylacetic acid |
| 144 | Z-4-methyl-3,6-heptadien-1-ol Chem. Abst. 66, 104730s | B | 2-[Z-1-(4-methylhepta-3,6-dienyl)-amino]benzoic acid |
| 145 | E(+)-2,6-dimethyl-4,7-octadien-2-ol Chem. Abst. 75, 49345d | B | 3-[E(+)-2-(2,6-dimethylocta-4,7-dienyl)amino]phenylacetic acid |
| 146 | Z(+)-2,6-dimethyl-4,7-octadien-2-ol Chem. Abst. 75, 49345d | B | 2-[Z(+)-2-(2,6-dimethylocta-4,7-dienyl)amino]benzoic acid |
| 147 | E-3,7-dimethyl-3,6-octadien-1-ol Chem. Abst. 67, 64554z | B | 3-[E-1-(3,7-dimethylocta-3,6-dienyl)amino]phenylacetic acid |
| 148 | E-3,7 dimethyl-3,6-octadien-1-ol | B | 2-[Z-1-(3,7-dimethylocta-3,6-dienyl)amino]benzoic acid |
| 149 | Z-3-methyl-3,7-octadien-1-ol Chem. Abst. 69, 65681x | B | 3-[E-1-(3-methylocta-3,7-dienyl)-amino]phenylacetic acid |
| 150 | Z-3-methyl-3,7-octadien-1-ol Chem. Abst. 69, 26681x | B | 2-[Z-1-(3-methylocta-3,7-dienyl)-amino]benzoic acid |
| 151 | E-2-methyl-4,8-nonadien-1-ol Chem. Abst. 73, 87253p | B | 3-[Z-1-(4,6-dimethylhepta-3,5-dienyl)amino]phenylacetic acid |
| 152 | E-3,7-dimethyl-3,7-octadien-1-ol Chem. Abst. 69, 26681x | B | 2-[E-1-(3,7-dimethylocta-3,7-dienylamino]phenylacetic acid |
| 153 | E-8-methyl-7-methylene-3-nonen-1-ol Chem. Abst. 70, 29098u | B | 3-[E-1-(8-methyl-7-methylenenon-3-enyl)-amino]benzoic acid |
| 154 | 2,4,9-trimethyl-4,8-decadien-1-ol Chem. Abst. 74, 99342s | B | 2-[2-(2,4,9-trimethyldeca-4,8-dienyl)amino]phenylacetic acid |
| 155 | E-2-methyl-4,9-decadien-1-ol Chem. Abst. 73, 87254g | B | 3-[E-2-(2-methyldeca-4,9-dienyl)amino]-benzoic acid |
| 156 | 2,6-dimethyl-5,7 octadien-2-ol Chem. Abst. 72, 37616t | B | 2-[2-(2,6-dimethylocta-5,7-dienyl)-amino]phenylacetic acid |
| 157 | E-3,7-dimethyl-4,6-octadien-1-ol Chem. Abst. 72, 121291r | B | 3-[E-1-(3,7-dimethylocta-4,6-dienyl)-amino]benzoic acid |
| 158 | Z-3,7-dimethyl-4,6-octadien-1-ol Chem. Abst. 72, 121291r | B | 2-[Z-1-(3,7-dimethylocta-4,6-dienyl)-amino]phenylacetic acid |
| 159 | E-4,7-octadien-1-ol Chem. Abst. 66, 28610k | B | 3-[E-1-(octa-4,7-dienyl)amino]benzoic acid |
| 160 | 5,8-nonadien-2-ol Chem. Abst. 68 28610k | B | 2-[2-(nona-5,8-dienyl)amino]phenylacetic acid |
| 161 | E-7-methyl-4,7-octadien-1-ol Chem. Abst. 66, 28619k | B | 3-[E-1-(7-methylocta-4,7-dienyl)-amino]benzoic acid |
| 162 | E-8-methyl-5,8-nonadien-2-ol Chem. Abst. 66, 28610k | B | 2-[E-2-(8 methylnona-5,8-dienyl)-amino]benzoic acid |
| 163 | E-6,10-dimethyl-5,9-undecadien-2-ol Chem. Abst. 73, 1331152f | B | 3-[E-2-(6,10 dimethylundeca-5,9-dienyl)amino]phenylacetic acid |
| 164 | 5,9,13-trimethyl-8,13-tetradecadien-2-ol Chem. Abst. 70, 28303v | B | 2-[6-(5,9,13-trimethyltetradeca-8,12-dienyl)amino]-benzoic acid |
| 165 | E-3,7,11-trimethyl 6,10-dodecadien-3-ol Chem. Abst. 69, 8333f | B | 3-[E-3-(3,7,11-trimethyldodeca-6,10-dienyl)amino]-phenylacetic acid |
| 166 | z-3,7,11-trimethyl-6,10-dodecadien-3-ol Chem. Abst. 69, 8333f | B | 2-[Z-3-(3,7,11-trimethyldodeca-6,10-dienyl)amino]-benzoic acid |
| 167 | 5,9-dimethyl-4,8-decadien-1-ol Chem. Abst. 74, 112233n | B | 3-[1-(5,9-dimethyldeca-4,8-dienyl)-amino]phenylacetic acid |
| 168 | 15-methanesulfonyloxy-1,11-pentadecadiene Ref. B | B | 2-[1-pentadeca-4,14-dienylamino)benzoic acid |
| 169 | 5,7-octadien-1-ol Chem. Abst. 68, 688503a | B | 3-[1-octa-5,7-dienylamino)phenylacetic acid |
| 170 | E-3,7-dimethyl-5,7-octadien-1-ol Chem. Abst. 72, P90672j | B | 2-[E-1(3,7-dimethocta-5,7-dienyl)-amino]benzoic acid |
| 171 | 6,10-dimethyl-5,9-undecadien-1-ol Chem. Abst. 71, 50248y | B | 3-[1-(6,10-dimethylundeca-5,9-dienyl)-amino]phenylacetic acid |
| 172 | 2,6,10-trimethyl-5,9-undecadien-1-ol Chem. Abst. 71, 50243t | B | 2-[1-(2,6,10-trimethylundeca-5,9-dienyl)amino]acetic acid |
| 173 | 10-propyl-5,9-tridecadien-1-ol Chem. Abst. 68, 39028u | B | 3-[1-(10-propyltrideca-5,9-dienyl)-amino]benzoic acid |
| 174 | 5,13-tetradecadien-2-ol Chem. Abst. 66, 35672k | B | 2-[1-tetradeca-5,13-dienylamino]phenylacetic acid |
| 175 | E-3,7,11-trimethyl-6,10-dedecadien-1-ol Chem. Abst. 69, 978z | B | 3-[1-(3,7,11-trimethyldodeca-6,-10-dienyl)amino]-benzoic acid |
| 176 | E-6,10,14-trimethyl-9,13-pendadecadien-2-ol Chem. Abst. 74, 53992j | B | 2-[E-2-(6,10,14-trimethylpentadeca-9,13-dienyl)amino]-phenylacetic acid |
| 177 | Z-6,10,14-trimethyl-9,13-pentadecadien-2-ol Chem. Abst. 74, 53992j | B | 3-8 Z-2-(6,10,14-trimethylpentadeca-9,13-dienyl)amino]-benzoic acid |

TABLE I-continued

| Example | Starting Material | Method | Product |
|---|---|---|---|
| 178 | Z,Z-9,12-octadecadien-2-ol Chem. Abst. 68, 92804V | B | 2-(1-octadeca-9,12-dienylamino)phenylacetic acid |
| 179 | E,Z-10,12-hexadecadien-1-ol Chem. Abst. 66 106133y | B | 3-[E,Z-1-hexadeca-10,12-dienylamino)benzoic acid |
| 180 | Z,E-10,12-hexadecadien-1-ol Chem. Abst. 66, P7956f | B | 2-[Z,E-1-hexadeca-10,12-dienylamino)phenylacetic acid |
| 181 | 2-methyl-2,3-butadien-1-ol Chem. Abst. 71, 30229n | B | 3-[1-(2-methylbuta-2,3-dienyl)amino]benzoic acid |
| 182 | 2-ethyl-2,3-buta-2,4-hexadien-2-ol Chem. Abst. 67, 535673e | B | 2-[1-(2-ethylbuta-2,3-dienyl)amino]phenylacetic acid |
| 183 | 2,3,5-trimethyl-3,4-hexadien-2-ol Chem. Abst. 72, 131953x | B | 2-[2-(2,3,5-trimethylhexa-3,4-dienyl)amino]benzoic acid |
| 184 | 3-isopropyl-2,4-dimethyl-4,5-hexadien-3-ol | B | 3-[3-(2,4-dimethylhexa-4,5-dienyl)-amino]phenylacetic acid |
| 185 | 2,5-dimethyl-3,4-hexadien-2-ol Chem. Abst. 68, 39152e | B | 2-[2-(2,5-dimethylhexa-3,4-dienyl)-amino]benzoic acid |
| 186 | 3,5-dimethyl-3,4-heptadien-2-ol Chem Abst. 72, 131953x | B | 3-[2-(3,5-dimethylhepta-3,4-dienyl)-amino]phenylacetic acid |
| 187 | 2-methyl-3,4-heptadien-2-ol Chem. Abst. 71, 38219g | B | 2-[2-(2-methylhepta-3,4-dienyl)amino]-benzoic acid |
| 188 | 2,3,5-trimetyl-3,4-heptadien-2-ol Chem. Abst. 72, 131953x | B | 3-[2-(2,3,5-trimethylhepta-3,4-dienyl)amino]phenylacetic acid |
| 189 | 3-t-butyl-2-methyl-3,4-octadien-2-ol Chem. Abst. 66, 75593s | B | 2-[2-(3-t-butyl-2-methylocta-3,4-dientyl)amino]benzoic acid |
| 190 | 2-ethyl-2,3-heptadien-1-ol Chem. Abst. 75, 63063s | B | 3-[1-(2-ethylhepta-2,3-dienyl)amino]-phenylacetic acid |
| 191 | 2-methyl-3,4-octadien-2-ol Chem. Abst. 75, 140175g | B | 2-[1-(2-methylocta-3,4-dienyl)amino]-benozic acid |
| 192 | 3-methyl-3,4-octadien-2-ol Chem. Abst. 66, 75593s | B | 3-[2-3-(3-methylocta-3,4-dienyl)-amino]phenylacetic acid |
| 193 | 5,6-decadien-4-ol Chem. Abst. 75, 76898t | B | 2-(4-deca-5,6-dienylamino)phenylacetic acid |
| 194 | 2,3-dimethyl-3,4-octadien-2-ol Chem. Abst. 66, 75593s | B | 3-[2-(2,3-dimethylocta-3,4-dienyl)-amino]benzoic acid |
| 195 | 4-ethyl-4,5-nonadien-3-ol Chem. Abst. 75, 63063s | B | 2-[3-(4-ethylnona-4,5-dienyl)amino]-phenylacetic acid |
| 196 | 2-methyl-3-propyl-3,4-octadien-2-ol Chem. Abst. 66, 65592v | B | 3-[2-(2-methyl-3-propylocta-3,4-dienyl)amino]benzoic acid |
| 197 | 2-methyl-3,4-nonadien-2-ol Chem. Abst. 75, 140173g | B | 2-[2-(2-methylnona-3,4-dienyl)amino]phenylacetic acid |
| 198 | 2,8-dimethyl-3,4-nonadien-2-ol Chem. Abst. 71, 38219g | B | 3-[2-(2,8-dimethylnona-3,4-dienyl)-aminobenzoic acid |
| 199 | 2-methyl-3,4-decadien-2-ol Chem. Abst. 75, 140173g | B | 2-]2-(2-methyldeca-3,4-dienyl)amino]-phenylacetic acid |
| 200 | 2,9-dimethyl-3,4-decadien-2-ol | B | 3-[2-(2,9-dimethyldeca-3,4-dienyl)-amino]benzoic acid |
| 201 | 2-methyl-3,4-dodecadien-2-ol Chem. Abst. 71, 38219g | B | 2-[2-(2-methyldodeca-3,4-dienyl)-aminophenylacetic acid |
| 202 | 2-methyl-3,4-tridecadien-1-ol Chem. Abst. 71, 38219g | B | 3-[2-(2-methyltrideca-3,4-dienlyl)-aminobenzoic acid |
| 203 | 4,5-hexadien-2-ol Chem. Abst. 75, 5152j | B | 2-(2-hexa-4,5-dienylamino)benzoic acid |
| 204 | 2-methyl-5,6-heptadien-3-ol Chem. Abst. 75, 5152j | B | 3-[2-(2-methylhepta-5,6-dienyl)amino]-phenylacetic acid |
| 205 | 3,3-dimethyl-4,5-hexadien-2-ol Chem. Abst. 69, 86256x | B | 2-[2-(3,3-dimethylhexa-4,5-dienyl)-aminobenzoic acid |
| 206 | 2,5-dimethyl-5,6-heptadien-3-ol Chem. Abst. 68, 86855w | B | 3-[2-(2,5-dimethylhepta-5,6-dienyl)-amino]phenylacetic acid |
| 207 | 2,2,5-trimethyl-3,4-hexadien-1-ol Chem. Abst. 71, 29767g | B | 2-[1-(2,2,5-trimethylhexa-3,4-dienyl)amino]benzoic acid |
| 208 | (+) 2,2-dimethyl-3,4-hexadien-1-ol Chem. Abst. 68, 58831s | B | 3-[1-(2,2-dimethylhexa-3,4-dienyl)-amino]phenylacetic acid |
| 209 | 3,4-hexadien-1-ol Chem. Abst. 66, 54943r | B | 2-[1-hexa-3,4-dienylamino)benzoic acid |
| 210 | 2,2,3,5-tetramethyl-3,4-hexadien-1-ol Chem. Abst. 71, 29767g | B | 3-[1-(2,2,3,5-tetramethylhexa-3,4-dienyl)amino]phenylacetic acid |
| 211 | 3,3,6-trimethyl-4,5-octadien-2-ol Chem. Abst. 69, 86256x | B | 2-[2-(3,3,6-trimethylocta-4,5-dienyl)-amino]benzoic acid |
| 212 | 2,5-dimethyl-5,6-heptadien-2-ol Chem. Abst. 69, 86256x | B | 3-[2-(2,5-dimethylhepta-5,6-dienyl)-amino]phenylacetic acid |
| 213 | 4-methyl-4-penten-2-yn-1-ol | B | 2-[1-(4-methylpent-4-en-2-ynyl)amino]-phenylacetic acid |
| 214 | 2-methyl-2-penten-2-yn-1-ol | B | 3-[1-(2-methylpent-2-en-4-ynyl)amino]-benzoic acid |
| 215 | 5-hexen-3-yn-2-ol | B | 2-[2-hex-5-en-3-ynylamino)phenylacetic acid |
| 216 | 7-octen-5-yn-4-ol Chem. Abst. 67, 113544g | B | 3-[4-oct-7-en-5-ynyl-amino)benzoic acid |
| 217 | 5-methyl-5-hexen-3-yn-2-ol | B | 2-[2-(5-methylhex-5-en-3-ynyl)amino]-phenylacetic acid |
| 218 | 2,5-dimethyl-1-nonen-3-yn-5-ol Chem. Abst. 69, 2433s | B | 3-[5-(2,5-dimethylnon-1-en-3-ynyl)-amino]benzoic acid |
| 219 | E-3-decen-1-yn-5-ol Chem. Abst. 75, 35042r | B | 2-(5-dec-3-en-1-ynyl-amino)phenylacetic acid |
| 220 | E-3-dodecen-1-yn-5-ol Chem. Abst. 75, 35042r | B | 3-(5-dodec-3-en-1-ynylamino)benzoic acid |
| 221 | 2-methyl-5-hexen-3-yn-2-ol Chem. Abst. 66, 75760v | B | 2-[2-(2-methylhex-5-en-3-ynyl)amino]-phenylacetic acid |

TABLE I-continued

| Example | Starting Material | Method | Product |
|---|---|---|---|
| 222 | 3-methyl-6-hepten-4-yn-3-ol Chem. Abst. 67, 113544g | B | 3-[3-(3-methylhept-6-en-4-ynyl)amino]-benzoic acid |
| 223 | 5-methyl-1-nonen-3-yn-5-ol Chem. Abst. 67, 43345s | B | 2-[5-(5-methylnon-1-en-3-ynyl)amino]-phenylacetic acid |
| 224 | 3-ethyl-6-hepten-4-yn-3-ol Chem. Abst. 71, 112202g | B | 3-[3-(3-ethylhept-6-en-4-ynyl)amino]-benzoic acid |
| 225 | 5-ethyl-1-nonen-3-yn-5-ol Chem. Abst. 72, 31124j | B | 2-[5-(5-ethylnon-1-en-3-ynyl)amino]-benzoic acid |
| 226 | 2,5-dimethyl-5-hexen-3-yn-2-ol Chem. Abst. 71, 112202g | B | 3-[2-(2,5-dimethylhex-5-en-3-ynyl)-amino]phenylacetic acid |
| 227 | 3,6-dimethyl-6-hepten-4-yn-3-ol Chem. Abst. 69, 96881m | B | 2-[2-(2,5-dimethylhex-5-en-3-ynyl)-amino]benzoic acid |
| 228 | 3-ethyl-6-methyl-6-hepten-4-yn-3-ol Chem. Abst. 71, 1122026 | B | 3-[3-(3-ethyl-6-methylhept-6-en-4-ynylamino]phenylacetic acid |
| 229 | 5-ethyl-2-methyl-3-yn-5-ol Chem. Abst. 69, 2433s | B | 2-[5-(5-ethyl-2-methyl-n-1-en-3-ynyl)amino]benzoic acid |
| 230 | 2-hexen-4-yn-1-ol Chem. Abst. 68, 77868a | B | 3-(1-(hex-2-en-4-ynylamino)phenyl-acetic acid |
| 231 | 4-methyl-4-hexen-2-yn-1-ol Chem. Abst. 66, 11524r | B | 2-[1-(4-methylhex-4-en-2-ynyl)amino]-benzoic acid |
| 232 | 5-hexen-2-yn-1-ol Chem. Abst. 71, 80580t | B | 3-(1-hex-5-en-2-ynyl-amino)phenylacetic acid |
| 233 | 5-methyl-5-hexen-2-yn-1-ol Chem. Abst. 70, 28152v | B | 2-[1-(5-methylhex-5-en-2-ynyl)amino]-benzoic acid |
| 234 | 5-hexen-3-yn-1-ol Chem. Abst. 73, 109833g | B | 3-(1-hex-5-en-3-ynylamino)phenyl-acetic acid |
| 235 | E-4-methyl-5-yn-1-ol Chem. Abst. 66, 104730s | B | 2-[E-1-(4-methyl-hept-3-en-5-ynyl)-amino]benzoic acid |
| 236 | z-4-methyl-5-yn-1-ol Chem. Abst. 66, 104730s | D | 2-[z-1-(4-methyl-hept-3-en-5-ynyl)-amino]phenylacetic acid |
| 237 | 3-hexen-5-yn-2-ol Chem. Abst. 75, 5152j | B | 3-(2-hex-3-en-5-ynylamino)benzoic acid |
| 238 | 6-methyl-6-hepten-4-yn-2-ol | B | 2-[2-(6-methylhept-6-en-4-ynyl)amino]-phenylacetic acid |
| 239 | 7-methyl-7-octen-5-yn-3-ol | B | 3-[3-(7-methyloct-7-en-5-ynyl)amino]-benzoic acid |
| 240 | 2,5-dimethyl-5-hexen-3-yn-2-ol | B | 2-[2-(2-dimethylhex-5-en-3-ynyl)amino]-phenylacetic acid |
| 241 | 3-methyl-6-octen-4-yn-3-ol Chem. Abst. 74, 41795j | B | 3-[3-(3-methyloct-6-en-4-ynyl)amino]-benzoic acid |
| 242 | 5-methyl-9-decen-6-yn-5-ol Chem. Abst. 73, 125271c | B | 2-[5-(5-methyldec-9-en-6-ynyl)amino]-phenylacetic acid |
| 243 | 2,5,5,6-tetramethyl-6-hepten-3-yn-2-ol Chem. Abst. 70, 10801w | B | 3-[2-(2,5,5,6-tetramethylhept-6-en-3-ynyl)amino]-benzoic acid |
| 244 | 3-ethyl-7-octen-4-yn-3-ol Chem. Abst. 73, 3762t | B | 2-[3-(3-ethyloct-7-en-4-ynyl)amino]-phenylacetic acid |
| 245 | 3-methyl-7-octen-4-yn-3-ol Chem. Abst. 73, 3762t | B | 3-[3-(3-methyloct-7-en-4-ynyl)amino]-benzoic acid |
| 246 | 2,6-dimethyl-6-hepten-3-yn-2-ol | B | 2-[2-(2,6-dimethylhept-6-en-3-ynyl)-amino]phenylacetic acid |
| | Chem. Abst. 73, 55677p | | |
| 247 | 3,6-diethyl-6-octen-4-yn-3-ol Chem. Abst. 68, 104850x | B | 3-[3-(3,6-diethyloct-6-en-4-ynyl)-amino]benzoic acid |
| 248 | 6-ethyl-6-octen-4-yn-2-ol Chem. Abst. 73, 19632z | B | 2-[2-(6-ethyloct-6-en-4-ynyl)amino]-benzoic acid |
| 249 | 6-methyl-6-hepten-2-yn-1-ol Chem. Abst. 72, 3587u | B | 3-[1-6-methylhept-6-en-2-ynyl)amino]-phenylacetic acid |
| 250 | E-4-methyl-3-hepten-6-yn-1-ol Chem. Abst. 66, 104730s | B | 2-[E-1-(4-methylhept-3-en-4-ynyl)-amino]benzoic acid |
| 251 | z-4-methyl-3-hepten-5-yn-1-ol Chem. | B | 3-[z-1-(4-methyl-hept-3-en-6-ynyl)-acid |
| 252 | E-2-octen-6-yn-1-ol Chem. Abst. 75, 63019g | B | 2-(E-1-oct-2-en-6-ynylamino)-benzoic acid |
| 253 | z-7-methyl-6-nonen-2-yn-1-ol Chem. Abst. 70, 78718j | B | 3-[z-1-(7-methylnon-6-en-2-ynyl)-aminophenylacetic acid |
| 254 | 8-methyl-7-methylene-3-nonyn-1-ol Chem. Abst. 66, 29098u | B | 2-[1-(8-methyl-1-methylenenon-3-ynyl)amino]benzoic acid |
| 255 | E-2-decen-4-yn-1-ol Chem. Abst. 67, 99692v | B | 3-(1-dec-2-en-4-ynylamino)phenyl-acetic acid |
| 256 | 4-methyl-4-decen-8-yn-1-ol Chem. Abst. 75, 110510x | B | 2-[1-(4-methyldec-4-en-8-ynyl)amino]-benzoic acid |
| 257 | E-2-undecen-4-yn-1-ol Chem. Abst. 66, 28594h | B | 3-(1-undec-2-en-4-ynylamino)phenyl-acetic acid |
| 258 | 6-methyl-5-undecen-2-yn-1-ol Chem. Abst. 71, p101399h | B | 2-[1-(6-methylundec-5-en-2-ynyl)amino]-benzoic acid |
| 259 | E-5-tetradecen-3-yn-1-ol Chem. Abst. 73, 87370z | B | 3-(E-1-tetradec-5-en-3-ynylamino)-phenylacetic acid |
| 260 | z-5-tetradecen-3-yn-1-ol Chem. Abst. 73, 87370z | B | 2-(z-1-tetradec-5-en-3-ynylamino)-phenylacetic acid |
| 261 | 10-propyl-9-tridecen-5-yn-1-ol Chem. Abst. 72, 12017k | B | 3-[1-(10-propyltridec-9-en-5-ynyl)-aminobenzoic acid |
| 262 | 17-octadecen-14-yn-1-ol Chem. Abst. 68, 39015n | B | 2-(1-octadec-17-en-14-ynylamino)phenyl-acetic acid |
| 263 | 2,4-dimethyl-1,4-hexadien-3-ol Chem. Abst. 74, 87269u | B | 3-[3-(2,4-dimethylhexa-1,4-dienyl)-aminobenzoic acid |
| 264 | 1,5-hexadien-3-ol Chem. Abst. 73, 44822f | B | 2-(3-hexa-1,5-dienylamino)phenyl-acetic acid |
| 265 | 3,5-dimethyl-1,5-hexadien-3-ol Chem. Abst. 67, 53415d | B | 3-[3-(3,5-dimethylhexa-1,5-dienyl)-aminobenzoic acid |
| 266 | 2,6-dimethyl-1,6-heptadien-3-ol Chem. Abst. 73, 87490p | B | 2-[3-(2,6-dimethylhepta-1,6-dienyl)-aminophenylacetic acid |
| 267 | E-2,6-dimethyl-1,6-octadien-3-ol Chem. Abst. 71, 61565a | B | 3-[E-3-(2,6-dimethylocta-1,6-dienyl)aminobenzoic acid |
| 268 | z-2,6-dimethyl-1,6-octadien-3-ol Chem. Abst. 71, 61565a | B | 2-[z-3-(2,6-dimethylocta-1,6-dienyl)aminophenylacetic acid |
| 269 | 3-ethyl-7-methyl-1,6-octadien-3-ol | B | 3-[3-(3-ethyl-7-methylocta-1,6-di- |

TABLE I-continued

| Example | Starting Material | Method | Product |
|---|---|---|---|
| 270 | 3-t-butyl-7-methyl-1,6-octadien-3-ol Chem. Abst. 66, p76192x | B | 2-[3-(3-1-butyl-7-methylocta-1,6-dienyl9amino]phenyl-acetic acid |
| 271 | 7,9-dimethyl-1,6-decadien-3-ol Chem. Abst. 71, p60078c | B | 2-[3-(7,9-dimethyl-deca-1,6-dienyl)-amino]benzoic acid |
| 272 | 3,7-dimethyl-1,6-decadien-3-ol Chem. Abst. 67, 2688n | B | 3-[3-(3,7-dimethyl-deca-1,6-dienyl)-amino]phenylacetic acid |
| 273 | 2-methyl-1,5-heptadien-4-ol Chem. Abst. 67, 53415d | B | 2-[4-(2-methylhepta-1,5-dienyl)amino]-benzoic acid |
| 274 | 4,6-dimethyl-1,5-heptadien-4-ol Chem. Abst. 67, 53415d | B | 3-[4-(4,6-dimethyl-hepta-1,5-dienyl)-amino]phenylacetic acid |
| 275 | E,E-3,4,5-trimethyl-2,5-heptadien-4-ol Chem. Abst. 72, 2823f | B | 2-[E,E-4-(3,4,5-tri-methylhepta-2,5-di-enyl)amino]benzoic acid |
| 276 | E,Z-3,4,5-trimethyl-2,5-heptadien-4-ol Chem. Abst. 72, 2823f | B | 3-[E,Z-4-(3,4,5-tri-methylhepta-2,5-di-enyl)amino]phenyl-acetic acid |
| 277 | z,z-3,4,5-trimethyl-2,5-heptadien-4-ol Chem. Abst. 72, 2823f | B | 2-[z,z-4-(3,4,5-tri-methylhepta-2,5-di-enyl)amino]benzoic acid |
| 278 | 2-methyl-2,9-decadien-5-ol Chem. Abst. 73, 87254q | B | 3-[5-(2-methyldeca-2,9-dienyl)amino]-phenylacetic acid |
| 279 | 8-methyl-1,7-nona-dien-5-ol Chem. Abst. 73, 87253p | B | 2-[5-(8-methylnona-1,7-dienyl)amino]-benzoic acid |
| 280 | 3,4,7,7-tetrameth-yl-1,5-octadien-4-ol Chem. Abst. 67, 63514z | B | 3-[5-(3,4,7,7-tetra-methylocta-1,5-dienyl)-enyl)amino]phenyl-acetic acid |
| 281 | 3,4-dimethylene-2-hexanol Chem. Abst. 69, 106850s | B | 2-[2-(3,4-dimethylene-hexyl)amino]benzoic acid |
| 282 | 3-methyl-2-methyl-ene-3-butene-1-ol Chem. Abst. 74, 42503z | B | 2-[1-(3-methyl-2-methylenebut-3-enyl)amino]phenyl-acetic acid |
| 283 | 2-methylene-3-buten-1-ol Chem. Abst. 73, p67478n | B | 3-[1-(2-methylene-but-3-enyl)amino]-benzoic acid |
| 284 | 3,3-dimethyl-2-methylene-4-penten-1-ol Chem. Abst. 74, 52962n | B | 2-[1-(3,3-demethyl-2-methylenepent-4-enyl)amino]phenyl-acetic acid |
| 285 | 2-methylene-3-meth-yl-4-hexen-1-ol Chem. Abst. 68 59021q | B | 3-[1-(2-methylene-3-methylhex-4-enyl)-amino]benzoic acid |
| 286 | 2,4-dimethyl-3-methylene-5-hexen-2-ol Chem. Abst. 72, 66299x | B | 2-[2-(2,4-dimethyl-3-methylenehex-5-enyl)amino]-phenylacetic acid |
| 287 | 2,4,4-trimethyl-3-methylene-5-hexen-2-ol Chem. Abst. 74 ,52962n | B | 3-[2-(2,4,4-tri-methyl-3-methylene-hex-5-enyl)amino]-benzoic acid |
| 288 | E-2-methyl-3-methyl-ene-5-hepten-2-ol Chem. Abst. 72, 132999d | B | 2 [E-2-(2-methyl-3-methylenehept-5-enyl)amino]phenyl-acetic acid |
| 289 | z-2-methyl-3-methyl-ene-5-hepten-2-ol Chem. Abst. 72, 132999d | B | 3-[z-2-(2-methyl-3-methylenehept-5-enyl)amino]benzoic acid |
| 290 | 2-dimethyl-1,3-methylene-5-hepten-2-ol Chem. Abst. 72, 132999d | B | 2-[2-(2,6-dimethyl-3-methylenehept-5-enyl)amino]phenyl-acetic acid |
| 291 | 3,7-dimethyl-2-methylene-6-octen-1-ol Chem. Abst. 68, 1114750d | B | 3-[1-(3,7-dimethyl-2-methyleneoct-6-enyl)amino]-benzoic acid |
| 292 | 3,7-dimethyl-2-methylene-7-octen-1-ol Chem. Abst. 70, p37191j | B | 2-[1-(3,7-dimethyl-2-methyleneoct-7-enyl)amino]-benzoic acid |
| 293 | 3-isopropylidene-2,5-dimethyl-4-hex-en-2-ol Chem. Abst. 74, 53105x | B | 3-[2-(3-isopropyl-idene-2,5-dimethyl-hex-4-enyl)amino]-phenylacetic acid |
| 294 | 2-methyl-6-methyl-ene-7-octen-4-ol Chem. Abst. 69, 10548y | B | 2-[4-(2-methyl-6-methyleneoct-7-enyl)amino]benzoic acid |
| 295 | 2-isopropylidene-5-methyl-4-hexene-1-ol Chem. Abst. 72, 132999d | B | 3-[1-(2-isopropyl-idene-5-methylhex-4-enyl)amino]phenyl-acetic acid |
| 296 | 7-methyl-3-methyl-ene-6-octen-1-ol Chem. Abst. 73, 131140a | B | 2-[1-(7-methyl-3-methyleneoct-6-enyl)amino]-benzoic acid |
| 297 | 2-methyl-6-methyl-ene-7-octen-2-ol Chem. Abst. 71, p61600h | B | 3-[2-(2-methyl-6-methyleneoct-6-enyl)amino]-phenylacetic acid |
| 298 | E-2-ethylidene-6-methyl-5-hepten-1-ol Chem. Abst. 68, 114750d | B | 2-[E-1-(2-ethyl-idene-6-methylhept-5-enyl)amino]benzoic acid |
| 299 | z-2-ethylidene-6-methyl-5-hepten-1-ol Chem. Abst. 68, 114750d | B | 3-[z-1-(2-ethyl-idene-6-methylhept-5-enyl)amino]phenyl-acetic acid |
| 300 | 2,5-dimethyl-3-vinyl-4-hexen-2-ol Chem. Abst. 69, 45983p | B | 2-[2-(2,5-dimethyl-3-vinylhex-4-enyl)-amino]benzoic acid |
| 301 | 2-isopropenyl-5-methyl-4-hexen-1-ol Chem. Abst. 68, 111190k | B | 3-[1-(2-isopropenyl-5-methylhex-4-enyl)-amino]phenylacetic acid |
| 302 | 2-vinyl-5-hepten-1-ol Chem. Abst. 75, p151673w | B | 3-[1-(2-vinylhept-5-enyl)amino]phenyl-acetic acid |
| 303 | 2-vinyl-6-hepten-1-ol Chem. Abst. 75, p15167w | B | 3-[1-(2-vinylhept-6-enyl)amino]benzoic acid |
| 304 | 2-(2-methylpropen-yl)-5-hexen-1-ol Chem. Abst. 68, 114750d | B | 2-[1-(2-methylpro-penylhex-5-enyl)-amino]phenylacetic acid |
| 305 | 7-methyl-3-vinyl-6-octen-1-ol Chem. Abst. 66, p115838j | B | 3-[1-(7-methyl-3-vinyloct-6-enyl)-amino]benzoic acid |
| 306 | 2-allyl-4-methyl-4-penten-1-ol Chem. Abst. 72, 21731r | B | 2-[1-2-allyl-4-methylpent-4-enyl)amino]phenyl-acetic acid |
| 307 | 3-methyl-5-undecen-1-yn-3-ol Chem. Abst. 71, p101399h | B | 3-[3-(3-methylundec-5-en-1-ynyl)amino]-benzoic acid |
| 308 | 3,4,8-trimethyl-8-nonen-1-yn-3-ol Chem. Abst. 68, 29184r | B | 2-[3-(3,4,8-tri-methylnon-8-en-1-ynylamino]phenyl-acetic acid |
| 309 | 1-dodecen-4-yn-3-ol Chem. Abst. 66, 75603v | B | 3-(dodec-1-en-4-ynylamino)benzoic acid |
| 310 | 11-dedecen-1-yn-3-ol Chem. Abst. 73, 120015n | B | 2-(3-dodec-11-en-1-ynylamino)phenyl-acetic acid |
| 311 | 1-undecen-5-yn-4-ol | B | 3-(4-undec-1-en- |

TABLE I-continued

| Example | Starting Material | Method | Product |
|---|---|---|---|
| | Chem. Abst. 69, 2432r | | 5-ynylamino)benzoic acid |
| 312 | 3,7-dimethyl-6-nonen-1-yn-3-ol Chem. Abst. 71, p91265v | B | 2-[3-(3,7-dimethyl-non-6-en-1-ynyl)-amino]phenylacetic acid |
| 313 | 7,7-dimethyl-1-nonen-8-yn-5-ol Chem. Abst. 74, 22939t | B | 2-[5-(7,7-dimethyl-non-1-en-8-ynyl)-amino]benzoic acid |
| 314 | 2,3-dimethyl-1-nonen-4-yn-3-ol Chem. Abst. 68, 39161g | B | 3-[3-(2,5-kimethyl-non-1-en-4-ynyl)-amino]phenylacetic acid |
| 315 | 3,7-dimethyl-7-octen-1-yn-3-ol Chem. Abst. 73, p7095a | B | 2-[3-(3,7-dimethyl-oct-7-en-1-ynyl)-amino]benzoic acid |
| 316 | 4,6-dimethyl-5-hepten-1-yn-4-ol Chem. Abst. 66, 95156e | B | 3-[3-(4,6-kimethyl-hept-5-en-1-ynyl)-amino]phenylacetic acid |
| 317 | 1-penten-4-yn-3-ol Chem. Abst. 74, p140935m | B | 2-(3-pent-1-en-4-ynylamino)benzoic acid |

PREPARATION OF ESTERS

Treatment of the acids of Examples 1-317 and 321-358 with trifluoracetic anhydride to provide the N-COCF$_3$ derivative, followed by treatment with thionyl chloride to provide the N-COCF$_3$ acid chloride, followed by treatment with one of the following alcohols, followed by removal of the N-COCF$_3$ group with 1 N sodium hydroxide solution at 20° C. provides the corresponding ester of the starting acid.

Alcohols: methanol, ethanol, 2-methoxyethanol, butanol, pentanol, cyclopentanol, cyclohexanol, 1,2-propanediol, 1,3-propanediol, ethylene glycol, glycerol, glycidol, methyl glycolate, ethyl glycolate, glycolic acid, 2-hydroxypropionic acid, 3-hydroxybutyric acid, 4-hydroxybutyric acid, glyceric acid, 3-diethylamino-1-propanol, 1-diethylamino-2-propanol, 3-dimethylamino-1-propanol, 2-diisopropylaminoethanol, 3-(4-methyl-1-piperazino)-1,2-propanediol, 3-methoxy-1,2-propanediol, N-piperidineethanol, N,N-diethylethanolamine.

EXAMPLE 319

Preparation of 2-[1-(2,3-methano)octylamino]phenylacetic acid

To a stirred mixture of 5 g. of zinc-copper couple prepared by the Shank-Shechter Method [R. S. Shank and H. Schehter, *J. Org. Chem.*, 24, 1825 (1959)], 0.02 g. of iodine, and 100 ml. of anhydrous ether is added 8.7 g. of (0.05 mol) of methylene iodide. The mixture is heated in the absence of atmospheric moisture until a spontaneous reaction begins as evidenced by continued refluxing of the ether when the heat source is removed. Upon completion of the exothermic reaction, the mixture is refluxed for 30 minutes, the heat is removed and to this mixture is added a solution of 5.4 g. (0.04 mol) of cis-2-octenol [L. P. Paquette and R. F. Eizember, *J. Am. Chem. Soc.*, 91, 7110 (1969)] in 10 ml. of anhydrous ether at a rate sufficient to maintain constant reflux. When the addition is complete, the mixture is refluxed for 3 hours. The flask is cooled and the mixture is filtered and the filtrate is washed with cold dilute hydrochloric acid and saturated sodium bicarbonate, dried and evaporated to give Z-1-hydroxymethyl-2-n-pentyl-cyclopropane.

Preparation of the tosylate by the method of Example 2, followed by condensation with ethyl 2-aminophenylacetate by the method of Example 2, followed by saponification by the method of Example 2 provides 2-[1-(2,3-methano)octylamino]phenylacetic acid.

EXAMPLE 320

Treatment of the indicated olefin of the Table II with zinc and diiodomethane by the method of Example 319 to produce the corresponding cyclopropyl compound followed by treatment of the halide with, for example, ethyl 2- or 3-aminophenylacetate or methyl 2- or 3-aminobenzoate by the method of Example 1, followed by saponification of the resulting ester by the method of Example 1, is productive, respectively, of a 2- or 3-(methanoalkyl)aminophenylacetic acid or a 2- or 3-(methanoalkyl)aminobenzoic acid of Table II (Method C).

Treatment of the olefinic alcohols of Table II with zinc and diiodomethane by the method of Example 319 will produce the corresponding cyclopropyl alkanols which upon treatment with methanesulfonic anhydride (Method of Example 2) will produce the corresponding methanesulfonate ester which upon treatment with, for example, ethyl 2- or 3-aminophenylacetate or methyl 2- or 3-aminobenzoate by the procedure of Example 2 followed by saponification will produce the 2- or 3-(methanoalkyl)aminophenylacetic acids or the 2- or 3-(methanoalkyl)aminobenzoic acids of Table II (Methods D).

TABLE II

| Example | Starting Material | Method | Product |
|---|---|---|---|
| 321 | 3-bromo-3-isopropyl-4-methyl-1-pentene Chem. Abst. 54, 4355a | C | 2-[3-(3-isopropyl-4-methyl-1,2-methanopentyl)amino]phenylacetic acid |
| 322 | 4-bromo-2-heptene Chem. Abst. 70, 67482x | C | 3-[4-(2,3-methanoheptyl)amino]benzoic acid |
| 323 | 4-bromo-2,4-dimethyl-2-hexene Chem. Abst. 70, 3169t | C | 2-[4-(2,4-dimethyl-2,3-methanohexyl)-amino]phenylacetic acid |
| 324 | 5-chloro-3,5-dimethyl-3-heptene Chem. Abst. 54, 1256e | C | 3-[5-(3,5-dimethyl-3,4-methanoheptyl)-amino]benzoic acid |
| 325 | z-1-hydroxy-2-hexadecene Ref. B | D | 2-[z-1-(2,3-methanohexadecyl)amino]-phenylacetic acid |
| 326 | E-1-hydroxy-2-hexadecene Ref. B | D | 2-[E-1-(2,3-methanohexadecyl)amino]-benzoic acid |
| 327 | 1-bromo-4-methyl-3-heptene Chem. Abst. 71, 102020q | C | 3-[1-(4-methyl-3,4-methanoheptyl)-amino]phenylacetic acid |
| 328 | 1-bromo-4-methyl-3-heptene Chem. Abst. 71, P101399h | C | 2-[1-(4-methyl-3,4-methanononyl)amino]-benzoic acid |
| 329 | E-7-bromo-3-heptene Chem. Abst. 74, 99419 f | C | 3-[E-1-(4,5-methanoheptyl)amino]phenylacetic acid |
| 330 | 1-bromo-5,9-dimethyl-4-decene Chem. Abst. 51, 8699g | C | 2-[1-(5,9-dimethyl-4,5-methanodecyl)-amino benzoic acid |
| 331 | 1-methanesulfonyloxy-4-tetradecene Ref. B | C | 3-[1-(4,5-methanotetradecyl)amino]-phenylacetic acid |
| 332 | 1-methanesulfonyloxy-4-hexadecene Ref. B | C | 2-[1-(4,5-methanohexadecyl)amino]-benzoic acid |
| 333 | 6-bromo-1-hexene Chem. Abst 66, | C | 3-[1-(5,6-methanohexyl)amino]phenyl- |

TABLE II-continued

| Example | Starting Material | Method | Product |
|---|---|---|---|
| | 2142j | | acetic acid |
| 334 | 6-bromo-2-methyl-1-hexene Chem. Abst. 75, 109624f | C | 2-[1-(5,6-methano-5-methylhexyl)amino]benzoic acid |
| 335 | 6-chloro-1-heptene Chem. Abst. 72, 31877g | C | 3-[2-(6,7-methanoheptyl)amino]phenylacetic acid |
| 336 | 6-bromo-2-methyl-2-heptene Chem. Abst. 54, 13166f | C | 2-[2-(5,6-methano-6-methylheptyl)amino]benzoic acid |
| 337 | 7-chloro-2-octene Chem. Abst. 75 129245m | C | 3-[2-(6,7,-methanooctyl)amino]phenylacetic acid |
| 338 | E-1-chloro-4-nonene Chem. Abst. 67, 32294y | C | 2-[E-1-(4,5-methanononyl)amino]phenylacetic acid |
| 339 | 7-bromo-1-heptene | C | 3-[1-(6,7-methanoheptyl)amino]benzoic acid |
| 340 | 7-chloro-1-octene Chem. Abst, 75, 129245m | C | 2-[2-(7,8-methanooctyl)amino]phenylacetic acid |
| 341 | 6-bromo-6-methyl-1-heptene Chem. Abst. 66, 94482w | C | 3-[1-(2-methyl-6,7-methanoheptyl)amino]benzoic acid |
| 342 | 6-chloro-2-methyl-1-heptene Chem. Abst. 75, 129245 | C | 2-[1-(6-methyl-6,7-methanoheptyl)amino]phenylacetic acid |
| 343 | E-8-bromo-2-octene Chem. Abst. 74, 99419f | C | 3-[1-(6,7-methanooctyl)benzoic acid |
| 344 | 8-bromo-2,6-dimethyl-2-octene Chem. Abst. 72, 90573c | C | 2-[1-(3,7-dimethyl-6,7-methanooctyl)amino]phenylacetic acid |
| 345 | 11-bromo-5-undecene Chem. Abst. 67, 73101b | C | 3-[1-(6,7-methanoundecyl)amino]benzoic acid |
| 346 | 8-bromo-1-octene Chem. Abst. 70, 10990g | C | 2-[1-(7,8-methanooctyl)amino]phenylacetic acid |
| 347 | R-8-iodo-7-methyl-1-octene Chem. Abst. 74, 12573e | C | 3-[1-(2-methyl-7,8-methanooctyl)amino]benzoic acid |
| 348 | 1-chloro-7-tetradecene Chem. Abst. 54, 22461h | C | 2-[1-(7,8-methanotetradecyl) amino]phenylacetic acid |
| 349 | 9-chloro-1-nonene Chem. Abst. 70, 114490k | C | 3-[1-(8,9-methanononyl)amino]benzoic acid |
| 350 | 1-bromo-8-heptadecene Chem. Abst. 52, 249d | C | 2-[1-(8,9-methanoheptadecyl)amino]benzoic acid |
| 351 | E-1-bromo-9-octadecene Chem. Abst. 70, 47799j | C | 3-[E-1-(9,10-methanooctadecyl)amino]phenylacetic acid |
| 352 | z-1-bromo-9-octadecene Chem. Abst. 70, 46779j | C | 2-[z-1-(9,10-methanooctadecyl)amino]benzoic acid |
| 353 | 11-chloro-1-undecene Chem. Abst. 66, P19046d | C | 3-[1-(10,11-methanoundecyl)amino]phenylacetic acid |
| 354 | 12-iodo-3,7,11-trimethyl-1-dodecene | C | 2-[1-(2,6,10-trimethyl-11,12-methanododecyl)amino]benzoic acid |
| 355 | 13-bromo-1-tridecene Chem. Abst. 67, 43348v | C | 3-[1-(12,13-methanotridecyl)amino]phenylacetic acid |
| 356 | 22-bromo-9-docosene Chem. Abst. 73, 44976j | C | 2-[1-(13,14-methanodocosyl)amino]benzoic acid |
| 357 | 16-methanesulfonyloxy-1-hexadecene Ref. B | C | 3-[1-(15,16-methanohexadecyl)amino]phenylacetic acid |
| 358 | 3-chloro-2,4,4-trimethyl-1-pentene Chem. Abst. 72, 1110811 | C | 1-[3-(2,4,4-trimethyl]-1,2-methanopentyl)amino]benzoic acid |

EXAMPLE 359

2,3-Dihydroxypropyl 2-(4-pentadecenyl)aminophenyl]acetate

A solution of 7.35 g. of 2-(4-pentadecenyl)aminophenylacetic acid in 50 ml. of hexamethylphosphoramide is treated with 4.80 g. of 25% aqueous sodium hydroxide followed by 11.0 g. of 3-chloro-1,2-propanediol and then is heated at 140° C. for 6 hours. The mixture is diluted with water and ether and filtered to yield a white solid. Recrystallization from acetonitrile and then from carbon tetrachloride affords the product as a white solid.

EXAMPLE 360

2,3-Dihydroxypropyl 3-(4-tetradecenylamino)phenylbutyrate

A mixture of 2.25 g. of methyl 3-(4-tetradecenylamino)phenylbutyrate, 280 mg. of glycerol, and 1.37 g. of p-touluenesulfonic acid is heated at 180° C. for 18 hours and then is partitioned between ether and 3% aqueous sodium carbonate solution. The ether layer is separated, dried, and evaporated to yield the product as a white solid.

EXAMPLE 361

2,3-Dihydroxypropyl 2-(4-tetradecenylamino)phenylpropionate

A solution of 11.8 g. of 2-(4-tetradecenylamino)phenylpropionic acid, 1.00 g. of glycerol, and 5.35 ml. of boron trifluoride etherate in 200 ml. of toluene is stirred under reflux for 48 hours. The solution is treated with an additional 5.35 ml. of boron trifluoride etherate and refluxing is continued for 120 hours. Dilution with water and methylene chloride followed by filtration affords the product as a white solid.

EXAMPLE 362

Preparation of 3-(allylamino)hydrocinnamic acid

A 4 g. sample of ethyl 3-(allylamino)hydrocinnamate is hydrolyzed with 1.6 g. 85% potassium hydroxide in 60 ml. 95% ethanol by refluxing the solution for 5 hours. The solution is cooled, diluted with 100 ml. water and acidified to pH 4.5 with 37% hydrochloric acid. The precipitate is collected, dried in vacuo and crystallized from acetone to yield the title compound as white powder.

EXAMPLE 363

Preparation of 1-methanesulfonyloxyoctadec-9-ene

To a mixture of 250 ml. of dichloromethane, 25 g. 1-hydroxyoctadec-9-ene and 16.7 g. of triethylamine cooled in an ice-salt bath to −10° C. is added dropwise, over 15 minutes, 18.9 g. of methanesulfonyl chloride. The mixture is cooled at −10° C. to −15° C. for 30 minutes and then washed with 300 ml. each of cold water, 10% hydrochloric acid, sodium carbonate solution and with saturated sodium chloride solution. The organic layer is dried with magnesium sulfate and concentrated in vacuo to give a pale yellow oil.

EXAMPLE 364

Preparation of ethyl
2-(1-pentadec-4-enylamino)phenylacetate

To a cold (−20°) stirred solution of 10.8 g. 1-hydroxypentadec-4-ene prepared by lithium aluminum hydride reduction of methyl tetradec-3-encarboxylate and 13.4 ml. triethylamine in 300 ml. ether is added dropwise 5.6 ml. methanesulfonyl chloride in 5 ml. of either. After addition is completed, the solution is warmed to room temperature, stirred for 30 minutes and filtered directly into a solution of 23.1 g. ethyl 2-aminophenyl acetate in 100 ml. ether. After 17 hours at room temperature, the precipitate is filtered and washed with several portions of methylene chloride. The organic solution is washed twice with 100 ml. water, 100 ml. brine, dried and evaporated. The tan residue is crystallized from ethanol and from acetonitrile to yield the title compound as white crystals.

EXAMPLE 365

Preparation of ethyl
3-(1-pentadeca-4,14-dienylamino)hydrocinnamate

A solution of 8.6 ethyl 3-aminohydrocinnamate, 9.77 g. 3,13-tetradecadien-1-carboxaldehyde and a few crystals of 2,4-dinitrobenzenesulfonic acid in 250 ml. toluene is refluxed under a Dean-Stark trap for 17 hours, whereupon the theoretical amount (0.8 ml.) water has been collected. The toluene is evaporated to yield ethyl 3-[3-(1-pentadeca-4,14-dienylideneaminophenyl]propionate as a crystalline mass.

To a mixture of 17.8 g. of the above compound in 250 ml. ethanol is added 1.68 g. sodium borohydride and the mixture is stirred at room temperature for 18 hours. Excess reagent is decomposed by addition of 10 ml. acetic acid. The solution is concentrated in vacuo and the residue is partitioned between toluene and aqueous potassium carbonate. After drying, the toluene is evaporated to yield a solid. Crystallization from acetonitrile and from ethanol affords the title compound as white crystals.

EXAMPLE 366

Preparation of ethyl
3-[2-(3,7,11-trimethyldodeca-2,6,10-trienylamino)-phenyl]propionate A mixture of 5.0 g. of ethyl 2-aminohydrocinnamate, 10.0 g. of 1-methanesulfonyloxy-3,7,11-triemethyl-dodeca-2,6,10-triene (prepared by the method of Example 363), 4.2 g. of anhydrous powdered potassium carbonate and 40 ml. hexamethylphosphoramide is heated to 80° C. for 17 hours. The mixture is then cooled, diluted with water and extracted with ethyl ether. The ether extracts are washed with water, dried and evaporated. The residue is recrystallized from ethanol yielding the title compound as white crystals.

EXAMPLE 367

Preparation of ethyl
2-[1-(6-decylhept-6-enyl)amino]cinnamate

A mixture of ethyl 2-aminocinnamate, 5.9 g. 6-decyl-hept-6-enylbromide and one equivalent of anhydrous powdered potassium carbonate in 50 ml. hexamethylphosphoramide is heated for 20 hours at 60° C. The mixture is then cooled, diluted with water and extracted with ether. The combined ether extracts are dried, filtered and evaporated. Crystallization from acetonitrile provides the title compound as white crystals.

TABLE III

The following 2- or 3-(substituted-amino)hydrocinnamates are prepared from the appropriate starting material by the method shown. Alcohols are converted to the corresponding mesylates by the method of Example 363.

| Example No. | Method of Example | 2- or 3-(Substituted-amino)hydrocinnamate |
|---|---|---|
| 368 | 364 | Ethyl 2-(allylamino)hydrocinnamate |
| 369 | 367 | Ethyl 3-(1-octadec-9-enylamino)hydrocinnamate |
| 370 | 365 | Ethyl 2-(1-pentadec-4-enylamino)-hydrocinnamate |
| 371 | 366 | Ethyl 3-(1-tetradec-4-enylamino)hydrocinnamate |
| 372 | 367 | Ethyl 2-(1-pentadec-4,14-dienylamino)-hydrocinnamate |
| 373 | 364 | Ethyl 3-[1-(3,7,11-trimethyldodeca-2,6,-10-trienyl)amino]hydrocinnamate |
| 374 | 366 | Ethyl 2-[1-(6-decylhept-6-enyl)amino]-hydrocinnamate |
| 375 | 364 | Ethyl 3-[4-(2,3-methanoheptyl)amino]-hydrocinnamate |

TABLE IV

The following 2- or 3-(substituted-amino)hydrocinnamic acids are prepared from the esters of Table III by the method of Example 362.

| Example No. | 2- or 3-(Substituted-amino)hydrocinnamic acid |
|---|---|
| 376 | 2-(Allylamino)hydrocinnamic acid |
| 377 | 3-(1-Octadec-9-enylamino)hydrocinnamic acid |
| 378 | 2-(1-Pentadec-4-enylamino)hydrocinnamic acid |
| 379 | 3-(1-Tetradec-4-enylamino)hydrocinnamic acid |
| 380 | 2-(1-Pentadec-4,14-dienylamino)hydrocinnamic acid |
| 381 | 3-[1-(3,7,11-Trimethyldodeca-2,6,10-trienyl)-amino]hydrocinnamic acid |
| 382 | 2-[1-(6-Decylhept-6-enyl)amino]hydrocinnamic acid |
| 383 | 3-[4-(2,3-Methanoheptyl)amino]hydrocinnamic acid |

TABLE V

The following 2- or 3-(substituted-amino)cinnamates are prepared from the appropriate starting materials by the methods shown. Alcohols are converted to their corresponding mesylates by the method of Example 363.

| Example No. | Method of Example | 2- or 3-(Substituted-amino)cinnamate |
|---|---|---|
| 384 | 364 | Ethyl 2-(allylamino)cinnamate |
| 385 | 367 | Ethyl 3-(1-octadec-9-enylamino)cinnamate |
| 386 | 365 | Ethyl 2-(1-pentadec-4-enylamino)-cinnamate |
| 387 | 366 | Ethyl 3-(1-tetradec-4-enylamino)-cinnamate |
| 388 | 367 | Ethyl 2-(1-pentadec-4,14-dienylamino)-cinnamate |
| 389 | 364 | Ethyl 3-[1-(3,7,11-trimethyldodica-2,6,-10-trienyl)amino]cinnamate |
| 390 | 366 | Ethyl 2-[1-(6-decylhept-6-enyl)amino]-cinnamate |
| 391 | 364 | Ethyl 3-[4-(2,3-methanoheptyl)amino]-cinnamate |

TABLE VI

The following 2- or 3-(substituted-amino)cinnamic acids are prepared from the esters of Table V by the method of Example 362.

| Example No. | 2- or 3-(Substituted-amino)cinnamic acid |
|---|---|
| 392 | 2-(Allylamino)cinnamic acid |
| 393 | 3-(1-Octadec-9-enylamino)cinnamic acid |
| 394 | 2-(1-Pentadec-4-enylamino)cinnamic acid |
| 395 | 3-(1-Tetradec-4-enylamino)cinnamic acid |
| 396 | 2-(1-Pentadec-4,14-dienylamino)cinnamic acid |
| 397 | 3-[1-(3,7,1-Trimethyldodeca-2,6,10-trienyl amino]cinnamic acid |
| 398 | 2-[1-(6-Decylhept-6-enyl)amino]cinnamic acid |
| 399 | 2-[4-(2,3-Methanoheptyl)amino]cinnamic acid |

TABLE VII

The following 2- or 3-(substituted-amino)phenylpropiolates are prepared from the appropriate starting materials by the methods shown. Alcohols are converted to their corresponding mesylates by the method of Example 363.

| Example No. | Method of Example | 2- or 3-(Substituted-amino)phenylpropiolate esters |
|---|---|---|
| 400 | 365 | Ethyl 2-(allylamino)phenylpropiolate |
| 401 | 367 | Ethyl 3-(1-octadec-9-enylamino)phenylpropiolate |
| 402 | 367 | Ethyl 2-(1-pentadec-4-enylamino)phenylpropiolate |
| 403 | 366 | Ethyl 3-(1-tetradec-4-enylamino)phenylpropiolate |
| 404 | 366 | Ethyl 2-(1-pentadeca-4,14-dienylamino)phenylpropiolate |
| 405 | 364 | Ethyl 3-[1-(3,7,11-trimethyldodeca-2,6,-10-trienyl)amino]phenylpropiolate |
| 406 | 364 | Ethyl 2-[1-(6-decylhept-6-enyl)amino]phenylpropiolate |
| 407 | 365 | Ethyl 3-[4-(2,3-methanoheptyl)amino]phenylpropiolate |

TABLE VIII

The following 2- or 3-(substituted-amino)phenylpropiolic acids are prepared from the esters of Table VII by the method of Example 362.

| Example No. | 2- or 3-(Substituted-amino)phenypropiolic acid |
|---|---|
| 408 | 2-(Allylamino)phenylpropiolic acid |
| 409 | 3-(1-Octadec-9-enylamino)phenylpropiolic acid |
| 410 | 2-(1-Pentadec-4-enylamino)phenylpropiolic acid |
| 411 | 3-(1-Tetradec-4-enylamino)phenylpropiolic acid |
| 412 | 2-(1-Pentadeca-4,14-dienylamino)phenylpropiolic acid |
| 413 | 3-[1-(3,7,11-Trimethyldodeca-2,6,10-trienyl)-amino]phenylpropiolic acid |
| 414 | 2-[1-(6-Decylhept-6-enyl)amino]phenylpropiolic acid |
| 415 | 3-[4-(2,3-Methanoheptyl)amino]phenylpropiolic acid |

TABLE IX

The following 2- or 3-(substituted-amino)phenylbutyrates are prepared from the appropriate mesylates by the method of Example 366. The requisite mesylates are prepared by the method of Example 363.

| Example No. | 2- or 3-(Substituted-amino)phenylbutyrate esters |
|---|---|
| 416 | Ethyl 2-(allylamino)phenylbutyrate |
| 417 | Ethyl 3-(1-octadec-9-enylamino)phenylbutyrate |
| 418 | Ethyl 2-(1-pentadec-4-enylamino)phenylbutyrate |
| 419 | Ethyl 3-(1-tetradec-4-enylamino)phenyl butyrate |
| 420 | Ethyl 2-(1-pentadeca-4,14-dienylamino)-phenylbutyrate |
| 421 | Ethyl 3-[1-(3,7,11-trimethyldodeca-2,6,10-trienyl)amino]phenylbutyrate |
| 422 | Ethyl 2-[1-(6-decylhept-6-enyl)amino]-phenylbutyrate |
| 423 | Ethyl 3-[4-(2,3-methanoheptyl)amino]-phenylbutyrate |

TABLE X

The following 2- or 3-(substituted-amino)phenylbutyric acids are prepared from the esters of Table IX by the method of Example 362.

| Example No. | 2- or 3-(Substituted-amino)phenybutyric acid |
|---|---|
| 424 | 2-(Allylamino)phenylbutyric acid |
| 425 | 3-(1-Octadec-9-enylamino)phenylbutyric acid |
| 426 | 2-(1-Pentadec-4-enylamino)phenylbutyric acid |
| 427 | 3-(1-Tetradec-4-enylamino)phenylbutyric acid |
| 428 | 2-(1-Pentadeca-4,14-dienylamino)phenylbutyric acid |
| 429 | 3-[1-(3,7,11-Trimethyldodeca-2,6,10-trienyl)-amino]phenylbutyric acid |
| 430 | 2-[1-(6-Decylhept-6-enyl)amino]phenylbutyric acid |
| 431 | 3-[4-(2,3-Methanoheptyl)amino]phenylbutyric acid |

EXAMPLE 432

Preparation of 2-[4-(2,3-methanoheptyl)amino]acetophenone

2-Aminoacetophenone is heated with 5 g. 1-methanesulfonyloxy-2,3-methanoheptane (prepared by the method of Example 363) in 50 ml. hexamethylphosphoramide containing anhydrous potassium carbonate (1.9 g.) for 16 hours a 100° C. The solution is cooled to room temperature, filtered to remove solids, and the filtrate is diluted with cold water (50 ml.). The amber solid so obtained is collected and washed with water. Recrystallization from ethanol followed by dichloromethane provides 2-[4-(2,3-methanoheptyl)amino]acetophenone.

TABLE XI

The following 2- or 3-(substituted-amino)acetophenones are prepared by the method of Example 432. The requisite mesylates are prepared by the method of Example 363.

| Example No. | 2- or 3-(Substituted-amino)acetophenone |
|---|---|
| 433 | 2-(Allylamino)acetophenone |
| 434 | 3-(1-Octadec-9-enylamino)acetophenone |
| 435 | 2-(1-Pentadec-4-enylamino)acetophenone |
| 436 | 3-(1-Tetradec-4-enylamino)acetophenone |
| 437 | 3-(1-Pentadeca-4,14-dienylamino)acetophenone |
| 438 | 2-[1-(3,7,11-Trimethyldodeca-2,6,10-trienyl)-amino]acetophenone |
| 439 | 3-[1-(6-Decylhept-6-enyl)amino]acetophenone |

| Example No. | 2- or 3-(Substituted-amino)acetophenone |
|---|---|
| 440 | 2-[4-(2,3-Methanoheptyl)amino]acetophenone |

EXAMPLE 441

Preparation of sodium 3-(allylamino)phenylacetate

A mixture of 3.62 g. of 3-(allylamino)phenylacetic acid and 25 ml. of ethanol water (9:1) containing 0.400 g. of sodium hydroxide is stirred for 4 hours. The mixture is filtered and the residue washed with 10 ml. of ethanol-water (9:1) and dried in vacuo for 24 hours to yield sodium 3-(allylamino)phenylacetate as a white solid.

EXAMPLE 442

Preparation of 2-(1-octadec-9-enylamino)phenylacetyl chloride

A cold solution of 25 g. 2-(1-octadec-9-enylamino)phenylacetic acid in 500 ml. dimethoxyethane methylene chloride (4:1) is prepared and dry hydrochloric acid is bubbled through the solution until no more precipitate forms. The solution is treated with 25 ml. thionyl chloride and refluxed until all of the precipitate has dissolved. The solvents are evaporated to yield the acid chloride hydrochloride as an orange, semi-crystalline mass.

EXAMPLE 443

Preparation of 2-(N-trifluoroacetyl-allylamino)phenylacetyl chloride

A stirred ice-cold suspension of 9 g. 2-(allylamino)phenylacetic acid in 100 ml. of dimethoxyethane and 16 ml. of pyridine is treated with 18 ml. of trifluoroacetic anhydride at 0° C. The solution is stirred for 30 minutes at room temperature and then diluted with 300 ml. ether and 100 g. ice. After stirring vigorously for 15 minutes, the phases are separated, the ether solution is washed with brine, dried and evaporated to a white, amorphous solid.

To a solution of 9.2 g. of the above solid in 30 ml. methylene chloride and 0.5 ml. dimethylformamide is added 5.7 ml. thionyl chloride. After 20 hours at reflux, the solvents are evaporated to yield 2-(N-trifluoroacetylallylamino)phenylacetyl chloride as a light yellow, mobile oil.

EXAMPLE 444

Preparation of 3-(N-carbobenzyloxy-allylamino)phenylacetyl chloride

To 15 g. 3-(allylamino)phenylacetic acid in 200 ml. warm chloroform is added a solution of 12 g. sodium carbonate in 150 ml. water. To the vigorously stirred solution is added 10 g. carbobenzyloxy chloride. After 2 hours stirring at 40° C., the layers are separated, washed three times with 1 N hydrochloric acid, dried, and evaorated to an oil. The oil is dissolved in 300 ml. toluene, treated with 15 ml. thionyl chloride and the solution is refluxed for 5 hours. The solvents are evaporated and the residue is dissolved three times in toluene, evaporating each time ultimately to yield 3-(N-carbobenzyloxy-allylamino)phenylacetyl chloride as a viscous, orange oil.

EXAMPLE 445

Preparation of 1-[3-(N-tert-butyloxycarbonyl)-1-tetradec-4-enylamino]phenylacetyl imidazole A solution of 10 g. 3-(1-tetradec-4-enylamino)phenylacetic acid in 100 ml. dioxane is treated with 4.0 g. tert-butylazidoformate and 10 ml. pyridine. After stirring at room temperature for 18 hours, the protected amidoacid is precipitated from solution by the addition of 150 ml. water. The solid is collected, thoroughly dried, and dissolved in 200 ml. of a mixture consisting of methylene chloride/dimethoxyethane/pyridine (1:4:1). This solution is stirred overnight at room temperature and the solvents are evaporated to yield 1-[3-(N-tert-butyloxycarbonyl)-tetradec-4-enyl-amino]phenylacetyl imidazole as an orange oil.

EXAMPLE 446

Preparation of diethyl 2-[1-tetradec-4-enylamino)benzoylmalonate

A solution of 26.6 g. of diethyl malonate and 10 ml. of 1,2-dimethoxyethane is added to a suspension of 4.0 g. of sodium hydride in 1,2-dimethoxyethane under argon. A solution of 17.3 g. of 2-(1-tetradec-4-enylamino)benzoyl chloride hydrochloride in 1,2-dimethoxyethane is then added. The reaction mixture is refluxed for 4.5 hours, cooled, poured on ice, acidified, and extracted with ether. The ether solution is washed with water and saturated sodium chloride solution, dried over anhydrous sodium sulfate and concentrated to dryness. Addition of a small amount of ethanol to the residue gives a solid which is filtered and discarded. The ethanol filtrate is concentrated and the residue is recrystallized from ether to yield diethyl 2-(1-tetradec-4-enylamino)benzoylmalonate.

EXAMPLE 447

Preparation of tert-butyl ethyl 3-(1-pentadeca-4,14-dienylamino)benzoylmalonate

A solution of 28.0 g. of tert-butyl ethyl malonate in 10 ml. of 1,2-dimethoxyethane is added to a suspension of 4.0 g. of sodium hydride in 1,2-dimethoxyethane under argon. A solution of 17.3 g. of 3-(1-pentadeca-4,14-dienylamino)benzoyl chloride hydrochloride in 1,2-dimethoxyethane is then added. The reaction mixture is refluxed for 5 hours, cooled, poured on ice and extracted with ether. The ether solution is washed with water and saturated sodium chloride solution, dried over anhydrous sodium sulfate and concentrated to dryness. The residue is then recrystallized from ether to yield tert-butyl ethyl 4-(1-pentadeca-4,14-dienylamino)-benzoylmalonate.

EXAMPLE 448

Preparation of ethyl 2-[3-(1-allylamino)benzoyl]acetoacetate

A solution of 21.6 g. of ethyl acetoacetate and 10 ml. of 1,2-dimethoxyethane is added to a suspension of 4.0 g. of sodium hydride in 1,2-dimethoxyethane under argon. A solution of 17.3 g. of 2-(1-allylamino)benzoyl chloride hydrochloride in 1,2-dimethoxyethane is then added. The reaction mixture is refluxed for 5 hours, cooled, poured on ice and extracted with ether. The ether solution is washed with water and saturated sodium chloride solution, dried over anhydrous sodium sulfate and concentrated to dryness. Recrystallization from ether affords ethyl 2-[2-(1-allylamino)benzoyl]acetoacetate as a white solid.

EXAMPLE 449

Preparation of ethyl 3-(1-tetradec-4-enylamino)benzoylacetate

A solution of 3.0 g. of tert-butyl ethyl 3-(1-tetradec-4-enylamino)benzoyl malonate 10 ml. of trifluoroacetic acid is warmed with stirring for 3 hours. The solution is poured onto ice and neutralized with potassium hydroxide. The resulting precipitate is collected by filtration, washed with water and dried. Recrystallization from chloroform affords ethyl 3-(1-tetradec-4-enylamino)-benzoylacetate.

EXAMPLE 450

Preparation of 2-(1-tetradec-4-enylamino)benzoylacetic acid

Two grams of ethyl 2-(1-tetradec-4-enylamino)benzoylacetate is added to a solution of potassium hydroxide in 50 ml. of 1:9 water-ethanol. The reaction mixture is stirred for 24 hours at room temperature. Careful neutralization with sulfuric acid gave a precipitate which is filtered, washed with water, and dried to yield 2-(1-tetradec-4-enylamino)benzoylacetic acid.

EXAMPLE 451

Preparation of 2'-(1-allylamino)-2-(methylsulfinyl)acetophenone

To a solution of 5.8 g. of dimethyl sulfoxide, dried over sieves, and 50 ml. of tetrahydrofuran is slowly added 28 ml. of n-butyllithium (2.4 M in hexane). To this mixture is added 10 g. of methyl 2-(1-allylamino)-benzoate in 200 ml. of tetrahydrofuran. After two hours, the reaction mixture is poured onto ice, acidified with dilute hydrochloric acid and quickly extracted with chloroform. The chloroform extract is washed with water and saturated sodium chloride solution, and dried over anhydrous sodium sulfate. Concentration afford a solid which is washed with 500 ml. of hot hexane, filtered while hot and then washed with hexane. The white solid is dried in vacuo to yield 2'-(1-allylamino)-2-(methylsulfinyl)acetophenone.

EXAMPLE 452

Preparation of 3'-(1-allylamino)-2-(phenylsulfonyl)acetophenone

A solution of 864 mg. of sodium hydride and 5.3 g. of methylphenylsulfone in 20 ml. of 1,2-dimethoxyethane is stirred at 6° C. for one hour under an atmosphere of argon. To this solution is added a solution of 5.0 g. of methyl 3-(1-allylamino)benzoate in 50 ml. of tetrahydrofuran and the reaction mixture is stirred at 60° C. for 1.5 hours. The mixture is cooled, poured onto ice, acidified with dilute hydrochloric acid to pH 3 and then extracted with chloroform. The organic layer is separated, washed with water and saturated sodium chloride solution, dried over anhydrous sodium sulfate and then concentrated to dryness. The crude solid is chromatographed on silica gel, eluted with methylene chloride to yield 3'-(1-allylamino)-2-(phenylsulfonyl)acetophenone.

EXAMPLE 453

Preparation of 2'-(1-cyclopentylethylamino)-2-(phenylsulfinyl)acetophenone

To a solution of 6.2 g. of methylphenylsulfoxide, dried over sieves, and 50 ml. of tetrahydrofuran is slowly added 28 ml. of n-butyllithium (2.4 M in hexane). To this mixture is added 10 g. of a solution of methyl 2-(1-allylamino)benzoate in 200 ml. of tetrahydrofuran. After two hours, the reaction mixture is poured onto ice, acidified with diluted hydrochloric acid and quickly extracted with chloroform. The chloroform layer is washed with water and saturated sodium chloride solution and dried over anhydrous sodium sulfate. Concentration affords a solid which is washed with 500 ml. of hot hexane, filtered while hot, and then washed with 50 ml. of hexane. The white solid is dried in vacuo yielding 2'-(1-allylamino)-2-(phenylsulfinyl)acetophenone.

EXAMPLE 454

Preparation of 3-[3'-(1-allylamino)benzoyl]-2,4-pentanedione

A solution of 28.4 g. of 2,4-pentanedione and 20 ml. of 1,2-dimethoxyethane is added to a suspension of 13.6 g. of sodium hydride in 220 ml. of 1,2-dimethoxyethane under argon. A solution of 28.7 g. of 3-(1-allylamino)-benzoylchloride hydrochloride in 1,2-dimethoxyethane is then added. The reaction mixture is stirred at room temperature for 12 hours, cooled, poured onto ice and extracted with ether. The ether solution is washed with water and saturated sodium chloride solution dried over anhydrous sodium sulfate and concentrated. The residue is then chromatographed over silica gel to yield 3-[3'-(1-allylamino)benzoyl]-2,4-pentanedione.

EXAMPLE 455

Preparation of methyl 3-[2-(1-allylamino)benzoyl]propionate

A mixture of 35 g. of 3-(2-acetamidobenzoyl)propionic acid, 700 ml. of methanol and 1.4 ml. of concentrated sulfuric acid is refluxed for 76 hours. The solution is cooled to 35° C. and poured onto 7 g. of anhydrous sodium acetate while stirring. The reaction mixture is stirred in an ice-bath. The solid is collected and washed with cold methanol to yield 3-(2-aminobenzoyl)propionate as a white solid. A mixture of this solid, 9.2 g. of 1-allylbromide and 4.2 g of potassium carbonte is stirred for 20 hours at 125° C. under nitrogen. The mixture is then cooled to 25° C. and 30 ml. of water is added. After stirring, the product is filtered and washed with water. Recrystallization from methanol affords methyl 3-[2-(1-allylamino)benzoyl]propionate as a white solid.

EXAMPLE 456

Preparation of 3-[3-(1-allylamino)benzoyl]propionic acid

A solution of 5.4 g. of methyl 3-[3-(1-allylamino)benzoyl]propionate is stirred with 5.4 g. of potassium hydroxide in 100 ml. of 95% ethanol for 3 hours at reflux. The reaction mixture is cooled, diluted with 50 ml. of ethanol and 100 ml. of water, neutralized with hydrochloric acid. The solution is cooled to room temperature and filtered. The white solid is washed with 50% aqueous ethanol and dried. The product is recrystallized from ethanol to yield 3-[3-(1-allylamino)benzoyl]-propionic acid.

TABLE XII

The following acetophenones are prepared by the noted methods from the carboxylic acids of Tables I or II or appropriate derivatives thereof which are obtained by the methods of Examples 442–445.

| Example No. | Method of Example | 2- or 3-(Substituted-amino)acetophenones |
|---|---|---|
| 457 | 446 | Diethyl 2-[(1-tetradec-4-enyl)amino]-benzoylmalonate |
| 458 | 447 | tert-Butyl ethyl 3-(1-allylamino)-benzoylmalonate |
| 459 | 448 | Ethyl 2-[2-(1-pentadec-4,14-dienyl-amino)benzoyl]acetoacetate |
| 460 | 449 | Ethyl 3-[1-(3,7,11-trimethyldodeca-2,6,-10-trienyl)amino]benzoylacetate |
| 461 | 450 | 2-(2,3-Methanoheptylamino]benzoyl-acetic acid |
| 462 | 451 | 3-[1-(6-Decylhept-6-enyl)amino]-2-(methylsulfonyl)acetophenone |
| 463 | 452 | 2'-(Allylamino)-2-(phenylsulfonyl)-acetophenone |
| 464 | 453 | 3'-(Proparygylamino)-2-(phenyl-sulfinyl)acetophenone |
| 465 | 454 | 3'[3-(2,3-Methanoheptylamino)benzoyl]-2,4-pentanedione |
| 466 | 455 | Methyl 3-[3-(allylamino)benzoyl]-propionate |
| 467 | 456 | 3-[2-(1-Pentadec-4-enylamino)benzoyl]-propionic acid |

EXAMPLE 468

Preparation of 2-[1-(2,3-methanoheptyl)amino]benzonitrile

2-Aminobenzonitrile (11.8 g.) and 1-iodo-2,3-methanoheptane (16.3 g.) are dissolved in hexamethylphosphoramide (100 ml.) and heated under nitrogen in an oil bath maintained at 120° C. for 22 hours. The reaction mixture is cooled to room temperature and water (100 ml.) is added gradually. The mixture is then chilled in an ice bath. The precipitate separated is filtered, washed thoroughly with water, and dried. It is then washed repeatedly with hexane and dried. Recrystallization from ether-hexane affords 2-[1-(2,3-methanoheptyl)amino]benzonitrile as pale yellow crystals.

EXAMPLE 469

Preparation of 3-(allylamino)benzaldehyde

Di-isobutylaluminum hydride (54 ml., 25% solution in toluene) is added with stirring to a solution of 12.1 g. of 3-(allylamino)benzonitrile under a nitrogen atmosphere. After addition is completed, the solution is stirred for one hour. A solution of methanol in toluene (50 ml., 1:1) is added over 30 minutes and the mixture is poured into 500 ml. vigorously stirred ice-cold 50% aqueous sulfuric acid. The mixture is filtered and the organic layer separated. The aqueous solution is extracted twice with toluene (100 ml.) and the combined organic layers are washed with aqueous sodium bicarbonate, dried over magnesium sulfate, decolorized with charcoal, filtered and evaporated in vacuo to give a light yellow crystalline solid. The product is recrystallized from dichloromethane/hexane giving colorless needles.

TABLE XIII

The following 2- or 3-(substituted-amino)benzonitriles are prepared by the method of Example 468.

| Example No. | 2- or 3-(Substituted-amino)benzonitrile |
|---|---|
| 470 | 2-(Allylamino)benzonitrile |
| 471 | 3-(1-Octadec-9-enylamino)benzonitrile |
| 472 | 2-(1-Pentadec-4-enylamino)benzonitrile |
| 473 | 3-(1-Tetradec-4-enylamino)benzonitrile |
| 474 | 2-(1-Pentadeca-4,14-dienylamino)benzonitrile |
| 475 | 3-[1-(3,7,11-Trimethyldodeca-2,6,10-trienyl)-amino]benzonitrile |
| 476 | 2-[1-(6-Decylhept-6-enyl)amino]benzonitrile |
| 477 | 3-[4-(2,3-Methanoheptyl)amino]benzonitrile |

TABLE XIV

The following 2- or 3-(substituted-amino)benzaldehydes are prepared from the corresponding benzonitriles of Table XIII by the method of Example 469.

| Example No. | 2- or 3-(Substituted-amino)benzaldehydes |
|---|---|
| 478 | 2-(Allylamino)benzaldehyde |
| 479 | 3-(1-Octadec-9-enylamino)benzaldehyde |
| 480 | 2-(1-Pentadec-4-enylamino)benzaldehyde |
| 481 | 3-(1-Tetradec-4-enylamino)benzaldehyde |
| 482 | 2-(1-Pentadeca-4,14-dienylamino)benzaldehyde |
| 483 | 3-[1-(3,7,11-Trimethyldodeca-2,6,10-trienyl)-amino]benzaldehyde |
| 484 | 2-[1-(6-Decylhept-6-enyl)amino]benzaldehyde |
| 485 | 3-[4-(2,3-Methanoheptyl)amino]benzaldehyde |

EXAMPLE 486

Preparation of 2,3-dihydroxypropyl 2-(allylamino)phenylacetate

A solution of 7.34 g. of 2-(allylamino)phenylacetic acid, 4.80 g. of 25% aqueous sodium hydroxide, and 12.6 g. of 3-iodo-1,2-propanediol in 50 ml. of hexamethylphosphoramide is stirred for 24 hours at ambient temperature, diluted with 100 ml. of ether and stirred for 5 days at ambient temperature. The mixture is treated with water and extracted with ether. The dried extracts are evaporated to yield 2,3-dihydroxypropyl 2-(allylamino)phenylacetate.

EXAMPLE 487

Preparation of methyl 3-(allylamino)phenylacetate

A solution of 20.7 g. of 3-(allylamino)phenylacetic acid in 25 ml. of hexamethylphosphoramide is added to a stirred mixture of 0.800 g. of sodium hydride (57% in mineral oil) and 25 ml. of hexamethylphosphoramide. The solution which forms after one hour is treated with 11.0 g. of methyl iodide and is then stirred at 25° C. for 18 hours. Dilution with water followed by filtration affords a white solid which is crystallized from ethanol to yield methyl 3-(allylamino)phenylacetate

EXAMPLE 488

Preparation of 3-hydroxypropyl 2-(allylamino)phenylacetate

A mixture of 2.25 g. of methyl 2-(allylamino)phenylacetate, 280 mg. of 1,3-propanediol and 1.37 g. p-toluenesulfonic acid is heated at 180° C. for 18 hours and then is partitioned between ether and 3% aqueous sodium carbonate solution. The ether layer is separated, dried, and evaporated to yield 3-hydroxypropyl 2-(allylamino)phenylacetate.

EXAMPLE 489

Preparation of 2-ethoxyethyl 3-(allylamino)phenylacetate

A solution of 11.8 g. of 3-(allylamino)phenylacetic acid, 1.00 g. of 2-ethoxyethanol and 5.35 ml. of boron trifluoride etherate in 200 ml. toluene is stirred under reflux for 48 hours. The solution is treated with an additional 5.35 ml. of boron trifluoride etherate and refluxing is continued for 120 hours. Dilution with water and methylene chloride followed by filtration affords 2-ethoxyethyl 3-(allylamino)phenylacetate.

EXAMPLE 490

Preparation of methyl 2-(allylamino)hydrocinnamate

A solution of 50.5 g. of 2-(allylamino)hydrocinnamic acid and 34.4 ml. of boron trifluoride etherate in 200 ml. of methanol is stirred under reflux for 44 hours, allowed to cool, and poured into 1.20 liters of ice-cold 5% aqueous sodium carbonate solution. The white solid is collected by filtration and recrystallized from benzene-ethanol to yield methyl 2-(allylamino)hydrocinnamate.

EXAMPLE 491

Preparation of 1-(methoxycarbonyl)propyl 3-(allylamino)hydrocinnamate

To a solution of 10.0 g. 3-(allylamino)hydrocinnamoyl chloride hydrochloride in 200 ml. methylene chloride is added dropwise a solution of 3 g. methyl 2-hydroxybutyrate and 5 g. triethylamine in 100 ml. ether. After 17 hours stirring at room temperature, the precipitate is collected and washed with several portions of ether. The ether solution is washed with water, dried and evaporated to yield 1-(methoxycarbonyl)propyl 3-(allylamino)hydrocinnamate as a white solid.

EXAMPLE 492

Preparation of 1-(ethoxycarbonyl)ethyl 2-(allylamino)phenylacetate

To a warm mixture of 7 g. sodium 2-(allylamino)phenylacetate in 100 ml. ethanol is added 4.7 g. ethyl 2-tosyloxypropionate. After 17 hours at reflux, the cooled solution is diluted with an equal volume of water and the resultant precipitate is filtered. After washing with cold ethanol and drying, the product is crystallized from acetonitrile to yield 1-(ethoxycarbonyl)ethyl 2-(allylamino)phenylacetate as colorless crystals.

EXAMPLE 493

Preparation of 1-carboxyethyl 3-(allylamino)phenylacetate

A flask containing 10.0 g. 3-(allylamino)phenylacetic acid, 3.3 g. lactic acid, 500 mg. toluenesulfonic acid and 500 ml. toluene equipped with a Soxhlet extractor charged with activated 4 Å Linde molecular sieves. The solution is refluxed for 24 hours during which time the Soxhlet extractor is charged twice more with fresh sieves. The hot solution is filtered and left to cool, whereupon 1-carboxyethyl 3-(allylamino)phenylacetate separates as off-white crystals.

EXAMPLE 494

Preparation of diethyl O-[2-(allylamino)phenylacetyl]tartrate

A mixture of 2-[N-trifluoroacetyl-(allylamino)]-phenylacetyl chloride and 1.2 g. triethylamine in 100 ml. warm ether is treated with 2.5 g. diethyl tartrate and refluxed for 24 hours. The hot solution is filtered, the residue is washed with hot ether, and the solution is evaporated. After treatment with aqueous methanolic potassium carbonate, the product is precipitated by acidification, filtered, and dried. Crystallization from acetone yields diethyl O-[2-(allylamino)phenylacetyl]tartrate as a white, crystalline solid.

EXAMPLE 495

Preparation of O-[3-(allylamino)phenylacetyl]malic acid

A warm solution of 3-[N-carbobenzyloxy-(allylamino]phenylacetyl chloride and 1.3 g. triethylamine in 100 ml. ether is treated with 2 g. malic acid. An immediate precipitate forms, but the mixture is refluxed for one hour and filtered while hot. The solid is washed several times with hot ether, then the ether is evaporated to yield a white solid. The product is dissolved in tetrahydrofuran (100 ml.) and hydrogenated over 600 mg. 10% palladium-on-carbon at 50 psi until hydrogen uptake stops. The catalyst is filtered, and the solution is evaporated. The residue is crystallized from acetic acid to yield O-[3-(allylamino)phenylacetyl]malic acid.

EXAMPLE 496

Preparation of 2-(ethoxycarbonyl)vinyl 2-(allylamino)phenylacetate

To a mixture containing 4.3 g. 1-[2-(N-t-butyloxycarbonyl-allylamino)phenylacetyl]imidazole 50 ml. 5 N sodium hydroxide is added 3 g. ethyl 2-formyl acetate. The solution is vigorously stirred for 24 hours. The layers are separated, and the chloroform solution is washed once with 50 ml. 1 N sodium hydroxide. The solvent is evaporated and the residue is heated for 30 minutes at 40° C. in 50 ml. anhydrous trifluoroacetic acid. The solvent is again evaporated and the oil is crystallized from acetone to yield light yellow crystals of 2-(ethoxycarbonyl)vinyl 2-(allylamino)phenylacetate.

TABLE XV

The following esters are prepared by the methods shown from the carboxylic acids of Tables I, II, IV, VI, VIII and X or appropriate derivatives thereof obtained by the methods of Examples 441–445.

| Example No. | Method of Example | Ester |
|---|---|---|
| 497 | 486 | 2,3-Dihydroxypropyl 2-(allylamino)-phenylacetate |
| 498 | 486 | 2,3-Dihydroxypropyl 3-(1-octadec-9-enylamino)hydrocinnamate |
| 499 | 486 | 2,3-Dihydroxypropyl 2-(1-pentadec-4-enylamino)cinnamate |
| 500 | 486 | 2,3-Dihydroxypropyl 3-(1-pentadec-4,14-dienylamino)phenylpropiolate |
| 501 | 486 | 2,3-Dihydroxypropyl 2-[1-(3,7,11-trimethyldodeca-2,6,10-trienyl-amino]butyrate |
| 502 | 487 | Methyl 3-[1-(6-decylhept-6-enyl) amino]phenylacetate |
| 503 | 487 | Methyl 2-[4-(2,3,methanoheptyl)- |

-continued

| Example No. | Method of Example | Ester |
|---|---|---|
| | | amino]hydrocinnamate |
| 504 | 487 | Methyl 3-(1-pentadeca-4,14-dienyl-amino)cinnamate |
| 505 | 487 | Methyl 2-(1-octadec-9-enylamino)-phenylpropiolate |
| 506 | 487 | Methyl 3-[4-(allylamino)phenyl]-butyrate |
| 507 | 488 | 2-Hydroxypropyl 2-(allylamino)-phenylacetate |
| 508 | 488 | 4-Hydroxybutyl 3-[1-(6-decylhept-6-enyl)amino]hydrocinnamate |
| 509 | 488 | 2-Hydroxypropyl 2-[1-(3,7,11-trimethyldodeca-2,6,10-trienyl)amino]-cinnamate |
| 510 | 488 | 3-Hydroxypropyl 3-[4-(2,3-methano-heptyl)amino)]phenylpropionate |
| 511 | 488 | 2-Hydroxyethyl 2-[1-(6-decylhept-6-enyl)amino]phenylbutyrate |
| 512 | 489 | 2-Methoxyethyl 3-(propargylamino)-phenylacetate |
| 513 | 489 | 2-Ethoxyethyl 2-(1-cyclopropyl-methylamino)propionate |
| 514 | 490 | Methyl 3-(allylamino)hydrocinnamate |
| 515 | 490 | Methyl 2-(3-cyclopropylpropyl-amino)cinnamate |
| 516 | 491 | 1-Methoxycarbonylpropyl 3-(1-pentadec-4,14-dienylamino)hydrocinnamate |
| 517 | 491 | 1-Ethoxycarbonylpropyl 2-[1-(6-decylhept-6-enyl)amino]phenylpropionate |
| 518 | 492 | 1-Ethoxycarbonylethyl 3-(1-pentadec-4-enylamino)phenylpropionate |
| 519 | 493 | 1-Carboxyethyl 2-(1-octadec-9-enylamino)phenylacetate |
| 520 | 493 | 1-Carboxyethyl 3-[2-(2-methylcyclopropylethylamino]cinnamate |
| 521 | 493 | 1-Carboxybutyl 2-(allylamino)-phenylpropionate |
| 522 | 493 | 1-Carboxyethyl 4-[3-(1-pentadec-4-ethylamino)phenyl]butyrate |
| 523 | 494 | Diethyl O-[2-(1-pentadec-4,14-dienylamino)phenylacetyl]tartrate |
| 524 | 495 | O-[3-(Allylamino)benzoyl]malic acid |
| 525 | 495 | O-[2-(cyclopropylmethylamino)-benzoyl]malic acid |
| 526 | 496 | 2-(Ethoxycarbonyl)vinyl 3-(but-2-enylamino)hydrocinnamate |
| 527 | 496 | 2-(Ethoxycarbonyl)vinyl 2-(allyl-amino)cinnamate |
| 528 | 496 | 2-(Ethoxycarbonyl)vinyl 3-(tetradec-4-amino)propiolate |
| 529 | 496 | 2-(Ethoxycarbonyl)vinyl 4-[2-(1-octadec-9-enylamino)phenylbutyrate |

EXAMPLE 530

Preparation of
2-(pentadec-4-enylamino)benzhydroxamic acid

To a suspension of 2-(pentadec-4-enylamino)benzoic acid (44 g.) in glyme (350 ml.) and pyridine (70 ml.) at 0° C. is added trifluoroacetic anhydride (67 ml., 100 g.) at such a rate as to maintain the temperature at 20°-30° C. The resulting solution is stirred at 10°-15° C. for 2 hours, then diluted with ether (499 ml.), cooled in an ice-bath and ice (100 gm.) is added. The mixture is stirred vigorously at ambient temperature for 1 hours. The acqueous layer is extracted with ether and the combined ether extracts are washed with water, brine, dried over sodium sulfate and concentrated in vacuo to provide 57 g. of 2-[N-trifluoroacetyl-N-(pentadec-4-enyl)amino]benzoic acid as an oil that solidifies upon standing.

The N-trifluoracetyl derivative (57 g.) is dissolved in thionyl chloride (300 ml.) and refluxed for 3 hours. After cooling, the mixture is diluted with toluene and concentrated in vacuo. The residue is diluted again with hot toluene and filtered. The toluene is concetrated in vacuo to provide 61 g. of 2-[N-trifluoroacetyl-N-(pentadec-4-enyl)amino]benzoyl chloride as an oil.

To a stirred solution of hydroxylamine hydrochloride (16 g.) in pyridine (75 ml.) and dichloromethane (35 ml.) is added dropwise the previously prepared benzoyl chloride derivative (11.5 g.) in dichloromethane (20 ml.). After 1 hour, the mixture is diluted with water and extracted with ether. The combined organic extract is then washed with water, brine, dried with sodium sulfate and contrated in vacuo to afford 2-[N-trifluoroacetyl-N-(pentadec-4-enyl)amino]benzhydroxamic acid as an oil.

A portion of this oil (0.9 g.) is dissolved in ethanol (20 ml.), 1 N sodium hydroxide solution is added, and the mixture is stirred at ambient temperature. The mixture is stirred at ambient temperature. The mixture is chilled and filtered to provide a white solid that is washed with ethanol. The white solid is recrystallized from hot ethanol to provide 2-(pentadec-4-enylamino)benzhydroxamic acid.

EXAMPLE 531

Preparation of Esters

Treatment of the acids of Examples 1-317 and 321-358 with trifluoracetic anhydride to provide the N-COCF$_3$ derivative, followed by treatment with thionyl chloride to provide the N-COCF$_3$ acid chloride, followed by treatment with one of the following alcohols, followed by removal of the N-COCF$_3$ group with sodium hydroxide by the method of Example 530 provides the corresponding ester of the starting acid.

Alcohols: benzyl alcohol, p-fluorobenzyl alcohol, p-bromobenzyl alcohol, p-chlorobenzyl alcohol, p-methoxybenxyl alcohol, m-chlorobenzyl alcohol, p-carboxybenzyl alcohol, phenol, p-fluorophenol, p-bromophenol, p-chlorophenol, p-methoxyphenol, p-carboxyphenol, 4-cyanophenol, 3-hydroxypyridine, 2-chloro-3-hydroxypyridine, 5-carboxy-3-hydroxypyridine.

EXAMPLE 532

Preparation of Amides

Treatment of the acids of Examples 1-317 and 321-358 with trifluoroacetic anhydride to provide the N-COCF$_3$ derivative, followed by treatment with thionyl chloride to provide the N-COCF$_3$ acid chloride, followed by treatment with one of the following amines, followed by removal of the N-COCF$_3$ group with sodium hydroxide by the method of Example 530 provides the corresponding amide of the starting acid.

Amines: β-alanine, allylamine, allylcyclohexylamine, aminoacetonitrile, α-aminoacetophenone, 2-amino-1-butanol, 3-aminobutyric acid, 4-aminobutyric acid, 1-amino-1-cyclopentanemethanol, 2-amino-5-diethylaminopentane, N-(2-aminoethyl)morpholine, N-(2-aminoethyl)piperazine, N-(2-aminoethyl)piperidine, 2-amino-2-ethyl-a,3-propanediol, 2-(2-aminoethyl)pyridine, N-(2-aminoethyl)pyrrolidine, DL-4-amino-3-hydroxybutyric acid, 5-aminolevulinic acid, aminoethanesulfonic acid, p-aminoethylbenzenesulfonamide, 2-amino-3-methyl-1-butanol, aminomethylcyclobutane, 4-(aminomethyl)cyclohexanecarbonitrile, 1-aminoethyl-1-cyclohexanol, aminomethylcyclopropane, 4-(aminomethyl)piperidine, 2-amino-2-methyl-1,3-propanediol, 2-amino-2-methyl-1-propanol, 2-(aminomethyl)-2-propanol, 2-aminomethylpyridine, 3-aminomethylpyridine, 4-aminomethylpyridine, 2-amino-1-phenyl-ethanol, 2-amino-3-phenyl-1-propanol, 3-amino-3-phenylpropionic acid, 3-amino-1,2-propanediol, 1-amino-2-propanol, N-(3-aminopropyl)-diethanolamine, N-(3-aminopropyl)morpholine, 1-(3-aminopropyl)-2-pipecoline, N-(3-aminopropyl)-2-pyrrolidinone, 5-aminovaleric acid, bis-(2-ethanolethyl)amine, bis-(2-methylallyl)amine, p-bromophenethylamine, 3-bromopropylamine hydrobromide, n-butylamine, sec-butylamine, tert-butylamine, 2-chlorobenzylamine, 3-chlorobenzylamine, 5-chlorobenzylamine, 2-chloroethylamine, 3-chloropropylamine, cyclobutylamine, cycloheptylamine, 1,3-cyclohexanebis(methylamine), cyclohexanemethylamine, cyclohexylamine, cyclopentylamine, cyclopropylamine, 3-(di-n-butylamino)propylamine, 1,5-dimethylhexylamine, α,4-dimethyl-3-hydroxyphenethylamine, 1,1-dimethylpropargylamine, 1,2-dimethylpropylamine, 1,2-diphenylethylamine, ethylamine, ethyl-3-aminobutyrate, ethyl-4-aminobutyrate, 2-(ethylamino)ethanol, 1-ethylpropylamine, 1-ethynylcyclohexamine, m-fluorobenzylamine, p-fluorobenzylamine, 2-fluoroethylamine, furfurylamine, n-heptylamine, isoamylamine, isopropylamine, m-methoxybenzylamine, p-methoxybenzylamine, 2-methoxyethylamine, o-methoxyphenthylamine, p-methoxyphenethylamine, N-methyl-β-alanine-nitrile, 2-methylallylamine, methylamine, methylaminoacetonitrile, 2-(methylaminoethanol, 2-methylbenzylamine, 3-methylbenzylamine, 4-methylbenzylamine, 4-methylbenzylamine, 1-methylbutylamine, 4-methylcyclohexylamine, 1-norepinephrine, 4-phenylbutylamine, 1-phenylcyclopropanemethylaine, trans-2-phenylcyclopropylamine, D(-)-α-phenylglycinol, 2phenylglycinonitrile, phenylpropanolamine, 3-phenyl-a-propylamine, monopropargylamine, propylamine, taurine, tetrahydrofurfurylamine, 1,2,3,4-tetrahydro-1-naphthylamine, 2-(p-tolyl)ethylamine, m-aminobenzoic acid, p-aminobenzoic acid, o-aminobenzyl alcohol, p-aminobenzyl alcohol, 3,5-dimethylpiperidine, 2-ethylpiperidine, 3-hydroxypiperidine, 4-hydroxypiperidine, 2-iminopiperidine, isonipecotamide, isonipecotic acid, methyl-4-oxo-3-piperidinecarboxylate, 2-methylpiperidine, 3-methylpiperidine, 4-methylpiperidine, nipecotamide, 4-phenylpiperidine, 4-phenyl-1,2,3,5-tetrahydropyridine, pipecolinic acid, piperidine, 2-piperidineethanol, 2-piperidinemethanol, 3-piperidinemethanol, 4-piperidinopiperidine, 4-piperidine, 1,2,3,6-tetrahydropyridine, 2,2,6,6-tetramethylpiperidine, 2,2,6,6-tetramethyl-4-piperidinol, 2,2,6,6-tetramethyl-4-piperidone, 4,4-trimethylenedipiperidine, 2-methylpiperidine, 3-methylpiperidine, 4-methylpiperidine, 4-phenylpiperidine, piperidine, morpholine, hexamethyleneimine, heptamethyleneimine, pentamethyleneimine, pyrrolidine, N-methylpiperazine, dl-alanine, hydrazine, N-acetylhydrazine, dl-valine, Δ³-piperidine, dl-leucine, 2-aminoisobutyric acid.

EXAMPLE 533

Preparation of N-[3-(9-Octadecenylamino)benzoyl]benzamide

Sodium hydride (1.0 g., 50% dispersion in mineral oil) is washed with hexane three times under nitrogen. To the dry sodium hydride is added 5 ml. of freshly distilled tetrahydrofuran. To this suspension is added a solution of 2.4 g. of benzamide in 5 ml. of tetrahydrofuran. After complete reaction (30 min.), a solution of 0.9 g. 3-[N-(trifluoracetyl-N-(9-octadecenyl)amino]benzoyl chloride (Example 530) in 3 ml. of tetrahydrofuran is added. After stirring at ambient temperature for 1 hour, the reaction mixture is poured into water and extracted twice with ether. The ether extracts are washed with water, brine, dried with sodium sulfate, and concentrated in vacuo. The residue is recrystallized from ether-acetonitrile (1:1) to provide N-{3-[N-trifluoracetyl-N-(9-octadecenyl)amino]benzoyl}benzamide.

The N-trifluoroacetyl compound is in turn treated with ethanol and 1 N sodium hydroxide and the mixture is stirred at ambient temperature for 6 hours. Chilling and filtration affords a white solid which is recrystallized from ethanol to yield N-[3-(9-octadecenylamino)-benzoyl]benzamide.

EXAMPLE 534

Preparation of N-[2- or 3-(substituted amino)benzoyl or phenylacetyl]benzamides

Treatment of the N-COCF$_3$ acid halides (prepared by the method of Example 530 from the corresponding acids of Examples 1–317 and 321–358) with benzamide and sodium hydride followed by removal of the N-COCF$_3$ group by the method of Example 533 is productive of the corresponding benzamides.

EXAMPLE 535

Preparation of 2-(4-pentadecenylamino)-N-(phenylsulfonyl)benzamide

A solution of 31.4 g. of benzenesulfonamide in 250 ml. of dry dimethylacetamide is added dropwise, with stirring and cooling, to a suspension of 5.5 g. of sodium hydride in 100 ml. of dry dimethylacetamide over 30 minutes at room temperature. Stirring is continued for a further 30 minutes. In the meantime, a mixture of 36.2 g. of 2-(4-pentadecenylamino)benzoic acid in 1200 ml. of methylene chloride, 300 ml. of dimethoxyethane, and 40 ml. of thionyl chloride is refluxed for 1 hour and 15 minutes. The solution is evaporated to an oil which is co-evaporated twice with added dioxane to remove excess thionyl chloride. To the resulting oily residue of 2-(4-pentadecenylamino)benzoyl chloride hydrochloride is added, in one portion, the previously prepared mixture of sodium benzenesulfonamide in dimethylacetamide. The mixture is stirred for 30 minutes, without cooling, and is then filtered through a bed of diatomaceous earth. The filtrate is poured into 2 l. of water, and 250 ml. of saturated sodium chloride solution is added to coagulate the precipitate. The mixture is filtered and the product is washed with water and partially air dried. The product is dissolved in methylene chloride, the mixture is filtered through diatomaceous earth, and brine is added to break the emulsion. The layers are separated, the organic phase is dried over anhydrous sodium sulfate and filtered through a bed of 300 g. of hydrous magnesium silicate. The product is eluted with an additional 3 l. of methylene chloride. The first approximately 1 l. of filtrate is set aside and the remainder is evaporated to dryness. The residue is crystallized three times from toluene and the product is dried in the Abderhalden at 65° C. to provide the title compound as colorless crystals.

EXAMPLE 536

Preparation of 2- or 3-(substituted amino)-N-(sulfonyl)benzamides or phenylacetamides Treatment of the acid chloride hydrochloride (prepared from the corresponding carboxylic acids of Examples 1–317 and 321–358 by the procedure of Example 539 with the following sulfonamides by the procedure of Example 535 is productive of the corresponding 2- or 3-(substituted amino)-N-(sulfonyl)benzamide or phenylacetamides. The sulfonamide starting materials are benzenesulfonamide, methanesulfonamide, p-methylphenylsulfonamide, p-nitrophenylsulfonamide, p-chlorophenylsulfonamide.

EXAMPLE 537

Preparation of N-trifluoroacetyl-2 or 3-(4-tetradecenylamino)benzoyl chloride

A stirred, ice-cold suspension of 9 g. (24.9 m moles) 2- or 3-(4-tetradecenylamino)benzoic acid in 100 ml. dimethoxy ethane and 16 ml. pyridine is treated with 18 ml. trifluoroacetic anhydride. The solution is stirred at 0° C. for 30 minutes at room temperature. The solution is diluted with 300 ml. ether and 100 g. ice. After stirring vigorously for 15 minutes, the phases are separated, the ether solution is washed with brine, dried and evaporated to a white amorphous solid.

To 9.2 g. of the above product in 30 ml. methylene chloride and 0.5 ml. dimethylformamide is added 5.7 ml. thionyl chloride. After 20 hours at reflux, the solvents are evaporated to yield the product as a light yellow, mobile oil.

EXAMPLE 538

Preparation of N-carbobenzyloxy-2 or 3-(4,14-pentadecadienylamino)benzoyl chloride To 15 g. of 2- or 3-(4,14-pentadecadienylamino)benzoic acid in 200 ml. warm chloroform is added 15 g. sodium carbonate in 150 ml. water. To the vigorously stirred mixture is added 10 g. carbobenzoyl chloride. After 2 hours stirring at 40° C., the layers are separated, the chloroform layer is washed three times with 1 N hydrochloric acid, dried, and the solvent evaporated to yield an oil. The oil is dissolved in 300 ml. toluene, treated with 15 ml. of thionyl chloride, and the solution is refluxed for 5 hours. The solvents are evaporated and the residue is dissolved three times in toluene, evaporating each time to yield a viscous, orange oil.

EXAMPLE 539

Preparation of 2- or 3-(4-tetradecenylamino)benzoyl chloride

A cold solution of 25 g. 2- or 3-(4-tetradecenylamino)benzoic acid in 500 ml. dimethoxyethane-methylene chloride (4:1) is prepared and dry hydrochloric acid is bubbled through the solution until no more precipitate forms.

The solution is treated with 25 ml. thionyl chloride and refluxed until all of the precipitate has dissolved. The solvents are evaporated to yield an orange, semicrystalline mass.

In an analogous manner, 2- or 3-(4-tetradecenylamino)phenylacetyl chloride is obtained from the corresponding phenylacetic acid.

EXAMPLE 540

Preparation of N-[2-(4-tetradecenylamino)benzoyl]alanine

A solution pf 4.75 g. of N-trifluoroacetyl-2-(tetradecenylamino)benzoyl chloride and 1.2 g. of triethylamine in 200 ml. of warm ether is treated with 1.55 g. alanine ethyl ester and refluxed for 24 hours. The hot solution is filtered, the residue is washed with hot ether, and the solvent is evaporated from the combined filtrate and washings. After treatment of the residue with aqueous methanolic potassium carbonate, the product is precipitated by acidification, filtered and dried. Crystallization from acetone yields the product as a white, crystalline solid.

EXAMPLE 541

Preparation of 1-{3-[N-(t-butyloxycarbonyl)-N-(4-tetradecenylamino)benzoyl]}imidazole A solution of 10 g. of 3-(4-tetradecenylamino)benzoic acid in 100 ml. dioxane is treated with 4.0 g. of t-butylazidoformate and 10 ml. pyridine. After stirring at room temperature for 18 hours, the protected amidoacid is precipitated from solution by addition of 150 ml. of water. The product is collected and thoroughly dried. The curde product is dissolved in 200 ml. of a mixture consisting of methylene chloride/dimethoxy ethane/pyridine (1:4:1), and to this is added 5.4 g. of 1,1'-carbonyldiimidazole. The solution is stirred overnight at room temperature and the solvents are evaporated to yield the title compound as a thick orange oil.

EXAMPLE 542

Preparation of 1-[2- or 3-(4,14-pentadecadienylamino)benzoyl]piperidine

To a warm solution of 2- or 3-[N-carbobenzoyloxy-4,14-pentadecadienylamino]benzoyl chloride and 1.3 g. of triethylamine in 100 ml. ether is added 1.2 g. of piperidine. An immediate precipitate forms, but the mixture is refluxed for one hour and filtered while hot. The solid is washed several time with hot ether, then the ether is evaporated from the combined filtrate and washings to yield a white solid. The product is dissolved in tetrahydrofuran (100 ml.) and hydrogenated over 600 mg. 10% palladium on carbon at 20 psi until hydrogen uptake stops. The catalyst is filtered. The solution is evaporated, and the residue is crystallized from acetic acid to yield the title compound as a crystalline mass.

Treatment of a corresponding 2- or 3-(substituted-amino)phenylacetyl chloride in an analagous manner yields the corresponding piperidide.

EXAMPLE 543

Preparation of 1-[2- or 3-(4,14-pentadecadienylamino)benzoyl]pyrrolidine

A solution of 6.0 g. of 2- or 3-[N-carbobenzyloxy-N-(4,14-pentadecadienylamino)]benzoyl chloride and 1.2 g. triethylamine in 100 ml. warm ether is treated with 1.1 g. of pyrrolidine. After 1 hour at reflux, the precipitate is filtered off and washed with warm ether. After evaporation of the combined filtrate and washings to dryness, the residue is dissolved in 50 ml. 30% hydrobromic acid in acetic acid and warmed at 50° C. for 2 hours. The solvents are evaporated and the product is partioned between methylene chloride and water. The layers are separated and the methylene chloride is evaporated. The residue is crystallized from acetone to yield colorless crystals.

Treatment of a corresponding 2- or 3-(substituted amino)phenylacetyl chloride in an analogous manner yields the corresponding pyrolidine.

EXAMPLE 544

Preparation of O-[2-(4,14-pentadecadienylamino)benzoyl]malic acid

A warm solution of N-carbobenzyloxy-2-(4,14-pentadecadienylamino)benzoyl chloride and 1.3 g. triethylamine in 100 ml. ether is treated with 2 g. malic acid. An immediate precipitate forms, but the mixture is refluxed for one hour and filtered while hot. The solid is washed several times with hot ether, then the ether is evaporated to yield a white solid. The product is dissolved in tetrahydrofuran (100 ml.) and hydrogenated over 600 mg. 10% palladium-on-carbon at 50 psi until hydrogen uptake stops. The catalyst is filtered. The solution is evaporated and the residue is crystallized from acetic acid to yield the title compound as white crystals.

EXAMPLE 545

Preparation of N-[2- or 3-(4-tetradecenylamino)benzoyl]alanine

A solution of 4.75 g. of N-trifluoroacetyl-2- or 3-(4-tetradecenylamino)benzoyl chloride and 1.2 g. of triethylamine in 200 ml. of warm ether is treated with 1.55 g. alanine ethyl ester and refluxed for 24 hours. The hot solution is filtered, the residue is washed with hot ether, and the combined filtrate and washings are evaporated. After treatment of the residue with aqueous methanolic potassium carbonate, the product is precipitated by acidification, filtered and dried. Crystallization from acetone yields the product a white, crystalline solid.

Treatment of a corresponding 2- or 3-(substituted amino)phenylacetyl chloride in an analagous manner yields the corresponding alanines.

EXAMPLE 546

Preparation of 4-chlorophenyl 2-(4-tetradecenylamino)benzoate

To a solution of 6.4 g. 4-chlorophenol and 7.6 g. triethylamine in 500 ml. methylene chloride is added 10.4 g. 2-(4-tetradecenylamino)benzoyl chloride hydrochloride in 250 ml. methylene chloride. After four hours at reflux, the solution is cooled, washed with water and dilute phosphoric acid, and dried. After passing the solution through a column of alumina, the solvent is evaporated and the residue is crystallized from diisopropyl ether.

EXAMPLE 547

Preparation of N-[2-(4-tetradecenylamino)benzoyl]-2-amino ethanesulfonic acid

To a stirred solution of 2.50 g. of taurine and 5.6 ml. of triethylamine in 22.5 ml. of water is added 5.55 g. of N-{2-[2,2,2-trifluoro-N-(4-tetradecenyl)acetamido]benzoyloxy}succinimide as a solution in 45 ml. of ethanol. After 24 hours, the mixture is treated with 20 ml. of 2.0 M sodium hydroxide and 25 ml. of water. After stirring for 10 minutes, the mixture is acidified with dilute hydrochloric acid, and the crude product is collected by filtration. Recrystallization affords the title compound as a white solid.

EXAMPLE 548

Preparation of 3-[3-(4-pentadecenylamino)benzoyl]-4-carboethoxy-thiazolidine

One-tenth mole of 3-(4-pentadecenylamino)benzoyl chloride hydrochloride in methylene chloride is added to a solution of 0.1 mole of ethyl thiazolidine-4-carboxylate in chloroform containing two equivalents of triethylamine. After 5 hours at 20° C. the solution is filtered and evaporated to a white solid which is recrystallized from acetonitrile.

EXAMPLE 549

Preparation of 3-[3-(4-pentadecenylamino)benzoyl]-4-carboxythiazolidine

By means of the alkaline hydrolysis method of Example 2 the ethyl ester of Example 548 is converted to the subject carboxylic acid. This acid is also prepared using the procedure of Example 548 except that the acylation of the thiazolidine-4-carboxylic acid is carried out in aqueous acetone sodium bicarbonate solution.

EXAMPLE 550

Preparation of N-[2- or 3-(4-pentadecenylamino)benzoyl]glycine

A mixture of 26.4 g. of ethyl N-[2- or 3-(4-pentadecenylamino)benzoyl]glycinate, 110 ml. of 1 N sodium hydroxide solution, and 100 ml. of ethanol is stirred at ambient temperature for 2 hours and then partially evaporated. The gaseous solution is washed with diethyl ether, acidified with 6 N hydrochloric acid, and filtered. The white solid is dried in vacuo and recrystallized from acetone.

Treatment of a corresponding 2- or 3-substituted-aminophenylacetyl chloride in an analogous manner yields the corresponding glycine.

EXAMPLE 551

Preparation of N-[3-(4-pentadecenylamino)benzoyl]-2,3-dihydroxypropylamine

To a mixture containing 4.3 g. of [N-(t-butyloxycarbonyl)-3-(4-pentadecenylamino)benzoyl]imidazole, 50 ml. of chloroform, and 50 ml. of 5 N sodium hydroxide is added 1.1 g. of 3-amino-1,2-propanediol. The mixture is vigorously stirred for 24 hours, the layers are separated, and the chloroform solution is washed once with 50 ml. of 1 N sodium hydroxide. The solvent is evaporated and the residue is heated for 30 minutes at 40° C. in 50 ml. of anhydrous trifluoroacetic acid. The solvent is again evaporated and the resulting oil is crystallized from acetone to yield the product as light yellow crystals.

EXAMPLE 552

Preparation of N-(3-bromopropyl)-2-(4-tetradecenylamino)benzamide

To a slurry of 21.80 g. of 3-bromopropylamine hydrobromide in 200 ml. of glyme at 3° C. is added a solution of 23.9 g. of 2-(4-tetradecenylamino)benzoyl chloride hydrochloride in 65 ml. of glyme, concurrently with 26 ml. of triethylamine diluted to 39 ml. with 1,2-dimethoxyethane. The solution is warmed to reflux and 0.2 g. of 4-dimethylaminopyridine is added. The solution is heated for four hours and cooled overnight. The solid is removed and the mother liquor diluted with 200 ml. of water to yield a solid which is crystallized from cyclohexane and recrystallized from acetonitrile to yield the product.

EXAMPLE 553

Preparation of
2-[3-(4-tetradecenylamino)phenyl]-5,6-dihydro-[4H]-1,3-oxazine

To 0.4 g. of sodium hydride in 100 ml. of 1,2-dimethoxyethane is added 2.14 g. of N-(3-bromopropyl)-3-(4-tetradecenylamino)benzamide and 12 ml. of triethylamine. The turbid solution is heated to reflux for 20 hours. The solution is diluted with 100 ml. of water and cooled overnight. The solid is collected, washed with water, crystallized from cyclohexane, and recrystallized from acetonitrile to yield the product.

EXAMPLE 554

Preparation of
2-[2-(4-tetradecenylamino)phenyl]oxazoline

To a slurry of 15 g. of 2-bromoethylamine hydrobromide in 150 ml. of 1,2-dimethoxyethane are added simultaneously solutions of 31 g. of 2-(4-tetradecenylamino)benzoyl chloride hydrochloride in 60 ml. of 1,2-dimethoxyethane and 50 cc. of triethylamine (dropwise). Upon addition of 0.5 g. of 4-dimethylaminopyridine the mixture is stirred at room temperature overnight. The solution is refluxed for one hour and filtered. The solid is oven dried and partitioned between methylene chloride and water. The layers are separated and the organic phase dried over magnesium sulfate. The organic layer is concentrated and the residue collected and crystallized from cyclohexane and recrystallized from acetonitrile to yield the product.

EXAMPLE 555

Preparation of tetrahydropyranyl
3-(4-tetradecenylamino)benzoate

A mixture of 7 g. 3-(4-tetradecenylamino)benzoic acid, 2 g. dihydropyran and 100 mg. anhydrous p-toluenesulfonic acid in 50 ml. toluene is stirred at room temperature for 20 hours. The solution is washed with saturated sodium bicarbonate, dried, and evaporated. The residue is collected and crystallized from methylcyclohexane to yield the product as white crystals.

EXAMPLE 556

Preparation of 3-pyridyl
2-(4-tetradecenylamino)benzoate

A 6 g. sample of 2-(4-tetradecenylamino)benzoic acid and 2.7 g. 1,1'-carbonydiimidazole in 50 ml. dry tetrahydrofuran is stirred for 2 hours. Then 1.58 g. 3-hydroxypyridine and a trace of sodium hydride catalyst is added and the reaction is refluxed for 3 hours. The solution cooled, filtered, and evaporated. The product is crystallized from isopropanol.

I claim:

1. An acid containing the organic radical (2,3-methanohept-4-ylamino) selected from the group consisting of 3-(2,3-methanohept-4-ylamino)benzoic acid, 3-[3-(2,3,-methanohept-4-ylamino)phenyl]propionic acid, 4-[3-(2,3,-methanohept-4-ylamino)phenyl]butyric acid, 3-[3-(2,3-methanohept-4-ylamino)phenyl]acrylic acid, 3-(2,3-methanohept-4-ylamino)phenylpropionic acid, 3-(2,3,-methanohept-4-ylamino)benzoylacetic acid, 3-[3-(2,3,-methanohept-4-ylamino)benzoyl]propionic acid, and 2-(2,3,-methanohept-4-ylamino)benzoylacetic acid.

2. A compound containing the organic radical (2,3-methanohept-4-ylamino) selected from the group consisting of 3-(2,3-methanohept-4-ylamino)benzaldehyde, 3-(2,3-methanohept-4-ylamino)acetophenone, and 2'-(2,3-methanohept-4-ylamino)-2-(methylsulfonyl)acetophenone.

3. An ester containing the organic radical (2,3-methanohept-4-ylamino) selected from the group consisting of 2-[2-(2,3-methanohept-4-ylamino)benzoyl]acetoacetate and 3-(2,3,-methanohept-4-ylamino)benzoylmalonate.

4. The compound according to claim 1, 3-(2,3-methanohept-4-ylamino)benzoic acid.

5. The compound according to claim 1, 3-[3-(2,3,-methanohept-4-ylamino)phenyl]propionic acid.

6. The compound according to claim 1, 4-[3-(2,3-methanohept-4-ylamino)phenyl]butyric acid.

7. The compound according to claim 1, 3-[3-(2,3,-methanohept-4-ylamino)phenyl]acrylic acid.

8. The compound according to claim 1, 3-(2,3-methanohept-4-ylamino)phenylpropionic acid.

9. The compound according to claim 1, 3-(2,3-methanohept-4-ylamino)benzaldehyde.

10. The compound according to claim 1, 3-(2,3-methanohept-4-ylamino)acetophenone.

11. The compound according to claim 1, 3-(2,3,-methanohept-4-ylamino)benzoylacetic acid.

12. The compound according to claim 2, ethyl 2-[2-(2,3-methanohept-4-ylamino)benzoyl]acetoacetate.

13. The compound according to claim 2, diethyl 3-(2,3,-methanohept-4-ylamino)benzoylmalonate.

14. The compound according to claim 1, 2'-(2,3-methanohept-4-ylamino)-2-(methylsulfonyl)acetophenone.

15. The compound according to claim 1, 3-[3-(2,3,-methanohept-4-ylamino)benzoyl]propionic acid.

16. The compound according to claim 1, 2-(2,3,-methanohept-4-ylamino)benzoylacetic acid.

* * * * *